US012616776B2

(12) United States Patent (10) Patent No.: US 12,616,776 B2
Matsusaki et al. (45) Date of Patent: *May 5, 2026

(54) THREE-DIMENSIONAL TISSUE BODY, METHOD FOR PRODUCING SAME, AND FORMATION AGENT FOR THREE-DIMENSIONAL TISSUE BODY

(71) Applicants: TOPPAN PRINTING CO., LTD., Tokyo (JP); OSAKA UNIVERSITY, Osaka (JP)

(72) Inventors: Michiya Matsusaki, Suita (JP); Shinji Irie, Tokyo (JP); Shiro Kitano, Tokyo (JP)

(73) Assignees: TOPPAN PRINTING CO., LTD., Tokyo (JP); OSAKA UNIVERSITY, Osaka (JP)

( * ) Notice: Subject to any disclaimer, the term of this patent is extended or adjusted under 35 U.S.C. 154(b) by 1147 days.

This patent is subject to a terminal disclaimer.

(21) Appl. No.: 17/502,496

(22) Filed: Oct. 15, 2021

(65) Prior Publication Data

US 2022/0133952 A1 May 5, 2022

Related U.S. Application Data

(63) Continuation of application No. 16/480,114, filed as application No. PCT/JP2018/003249 on Jan. 31, 2018, now Pat. No. 11,179,495.

(30) Foreign Application Priority Data

Jan. 31, 2017 (JP) ................................. 2017-015958
Sep. 4, 2017 (JP) ................................. 2017-169834

(51) Int. Cl.
| | |
|---|---|
| *A61L 27/24* | (2006.01) |
| *A61L 27/38* | (2006.01) |
| *A61L 27/44* | (2006.01) |
| *A61L 27/54* | (2006.01) |
| *A61L 31/04* | (2006.01) |
| *C12N 5/00* | (2006.01) |

(52) U.S. Cl.
CPC ............... *A61L 27/24* (2013.01); *A61L 27/38* (2013.01); *A61L 27/3808* (2013.01); *A61L 27/3813* (2013.01); *A61L 27/3826* (2013.01); *A61L 27/44* (2013.01); *A61L 27/54* (2013.01); *A61L 31/044* (2013.01); *C12N 5/0068* (2013.01); *A61L 2430/20* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 4,511,653 | A | 4/1985 | Play |
| 7,201,917 | B2 | 4/2007 | Malavlya |
| 2005/0129730 | A1 | 6/2005 | Pang |
| 2005/0288796 | A1 | 12/2005 | Awad |
| 2007/0269476 | A1 | 11/2007 | Voytik-Harbin |
| 2012/0121793 | A1 | 5/2012 | Chang |
| 2016/0122723 | A1 | 5/2016 | Retting et al. |
| 2016/0251626 | A1 | 9/2016 | Akashi et al. |
| 2017/0232144 | A1 | 8/2017 | Kelly |

FOREIGN PATENT DOCUMENTS

| | | |
|---|---|---|
| JP | 2010-529177 | 8/2010 |
| JP | 2010-273847 | 12/2010 |
| JP | 2012-115254 | 6/2012 |
| WO | WO 2006/011296 A1 | 2/2006 |
| WO | WO 2009/007531 A2 | 1/2009 |
| WO | WO 2015/072164 A1 | 5/2015 |
| WO | WO 2016/027853 A1 | 2/2016 |
| WO | WO 2016/093362 A1 | 6/2016 |
| WO | WO 2016/143669 A1 | 9/2016 |
| WO | WO 2011/139228 A1 | 11/2021 |

OTHER PUBLICATIONS

Pei-Leun Kang et al.; "Nano-sized collagen I molecules enhanced the differentiation of rat mesenchymal stem cell into cardiomyocytes"; Society for Biomaterials; Mar. 5, 2013; p. 20161588, 085725, 2808-2816; (9 pages).
A. Bertolo et al.; "Injectable Microcarriers as Human Mesenchymal Stem Cell Support and Their Application for Cartilage and Degenerated Intervertebral Disc Repair"; European Cells and Materials vol. 29, 2015 (pp. 70-81); ISSN 1473-2262; (12 pages).
Office Action dated Mar. 1, 2022 in Japanese Patent Application No. 2020-155648 (3 pages).
Shulamit Levenberg et al., "Engineering vascularized skeletal muscle tissue", Nature Biotechnology, Jul. 2005, vol. 23, No. 7, pp. 879-884.
International Search Report mailed on May 1, 2018 in corresponding International Patent Application No. PCT/JP2018/003249.
English Translation by WIPO of the International Preliminary Report on Patentability dated Aug. 15, 2019 in corresponding International Patent Application No. PCT/JP2018/003249.
Japanese Patent Office Action issued in Japanese Patent Application No. 2018-565614 dated Oct. 1, 2019 (4 pages).
Extended European Search Report dated Sep. 10, 2020 in European Patent Application No. 18747101.6; 7 pages.

(Continued)

*Primary Examiner* — Allison M Fox
(74) *Attorney, Agent, or Firm* — STAAS & HALSEY LLP

(57) ABSTRACT

A method may comprises bringing cells suspended in an aqueous medium into contact with a plurality of fragmented collagen pieces and, after the cells brought into contact with the plurality of fragmented collagen pieces and the plurality of fragmented collagen pieces are concentrated, culturing the cells brought into contact with the fragmented collagen pieces, with the plurality of fragmented collagen pieces, to form a three-dimensional tissue.

17 Claims, 15 Drawing Sheets

(56) References Cited

OTHER PUBLICATIONS

Yuto Amano et al., "Development of vascularized iPSC derived from 3D-cardiomyocyte tissues by filtration Layer-by-Layer technique and their application for pharmaceutical assays"; Acta Biomaterialia 33 (2016) 110-121; 12 pages.

Jeroen Eyckmans et al., "3D culture models of tissues under tension" Special Issue: 3D Cell Biology; Journal of Cell Science (2017) 130, 63-70 doi: 10.1242/jcs.198630; 8 pages.

Kuo et al.; "Preparation of nano-sized collagen I and collagen II particles" The $2^{nd}$ International Conference on Bioinformatics and Biomedical Engineering (ICBBE), 2008, pp. 1417-1419.

Non-Final Office Action dated Nov. 8, 2019 in parent U.S. Appl. No. 16/480,119 (17 pages).

Final Office Action dated Apr. 28, 2020 in parent U.S. Appl. No. 16/480,114 (19 pages).

Advisory Action dated Aug. 6, 2020 in parent U.S. Appl. No. 16/480,114 (5 pages).

Non-Final Office Action dated Feb. 16, 2021 in parent U.S. Appl. No. 16/480,114 (14 pages).

Notice of Allowance mailed Jul. 16, 2021 in parent U.S. Appl. No. 16/480,114 (13 pages).

Lindberg et al.; Burns 2001; 27: 254-266 (Year: 2001).

Sochaga et al.; Tissue Engineering, Jul. 2006, 12(7): 1851-1863. (year: 2006).

Bueno et al.; Journal of Biotechnology, 2007, 129. 516-531 (Year: 2007).

Ma et al; Journal of Biomedicine and Biotechnology, 2011, Article ID 812135, 9 pages. (Year: 2011).

U.S. Appl. No. 16/480,114, filed Jul. 23, 2019, Michiya Matsusaki et al.

Fragmented collagen   NHDF   HUVEC

Seeded

Cultured together with the fragmented collagen

Cultured for 7 days

Three-dimensional tissue containing capillaries

CD31

1 mm

*Fig. 6A*      *Fig. 6B*
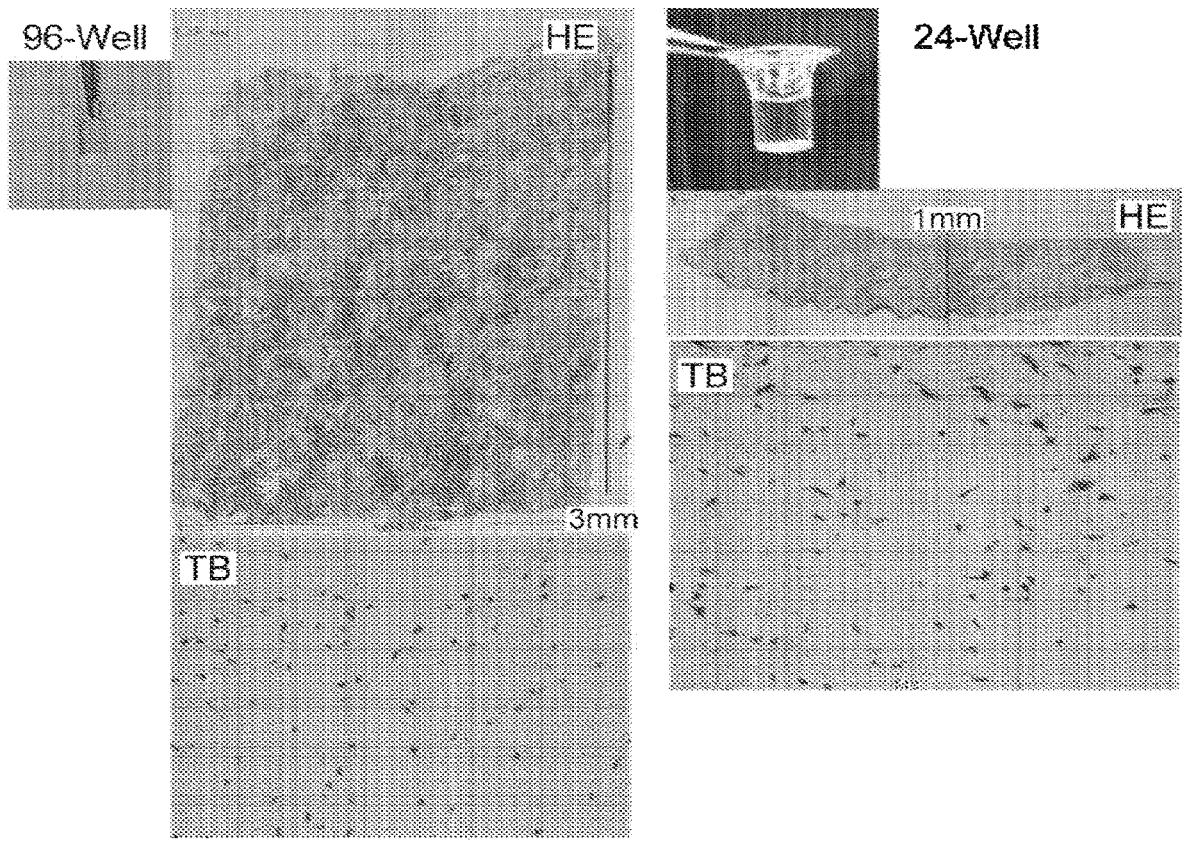

Day 1                    Day 2                    Day 3

Height                   Height                   Height
5.9 mm                   5.9 mm                   5.4 mm
(100%)                   (100%)                   (91%)

Day 1                    Day 2                    Day 6

THREE-DIMENSIONAL TISSUE BODY, METHOD FOR PRODUCING SAME, AND FORMATION AGENT FOR THREE-DIMENSIONAL TISSUE BODY

CROSS-REFERENCE TO RELATED APPLICATIONS

This application is a continuation application of U.S. patent application Ser. No. 16/480,114, filed on Jul. 23, 2019, which is a U.S. National Stage Application under 35 U.S.C. § 371 of PCT International Application No. PCT/JP2018/003249, filed on Jan. 31, 2018, which claims the foreign priority benefit under 35 U.S.C. § 119 of Japanese Patent Application No. 2017-169834, filed Sep. 4, 2017, and Japanese Patent Application No. 2017-015958, filed on Jan. 31, 2017, both in the Japanese Patent Office. The entire contents of the U.S. patent application Ser. No. 16/480,114, PCT International Application No. PCT/JP2018/003249, Japanese Patent Application No. 2017-169834, and Japanese Patent Application No. 2017-015958 are hereby incorporated by reference.

TECHNICAL FIELD

The present invention relates to a three-dimensional tissue, a method for producing the same, and a formation agent for the three-dimensional tissue.

BACKGROUND ART

Recently, techniques for ex vivo construction of a cell-based three-dimensional tissue have been developed. Proposed are, for instance, a method for producing a three-dimensional tissue by culturing cells coated such that the whole surface of each cultured cell is coated with an adhesion membrane (Patent Literature 1); and a method for producing a three-dimensional tissue by seeding cells on a scaffold made of a material such as poly-lactic acid (Non Patent Literature 1). In addition, the present inventors have proposed before a method for producing a three-dimensional tissue, comprising the step of three-dimensionally arranging cells coated with a collagen-containing film to form a three-dimensional tissue (Patent Literature 2); and a method for producing a three-dimensional tissue, comprising the step of forming a coated cell having a coating film on the cell surface and the step of three-dimensionally arranging the coated cell, wherein forming the coated cell includes immersing a cell in a liquid containing a coating film component and separating the immersed cell and the liquid containing the coating film component with a liquid permeable membrane (Patent Literature 3).

Such three-dimensional tissue bodies should be used as graft materials and alternatives for experimental animals, etc.

CITATION LIST

Patent Literature

Patent Literature 1: Japanese Unexamined Patent Publication No. 2012-115254
Patent Literature 2: International Publication No. WO 2015/072164
Patent Literature 3: International Publication No. WO 2016/027853

Non Patent Literature

Non Patent Literature 1: Nature Biotechnology, 2005, Vol. 23, NO. 7, p. 879-884

SUMMARY OF INVENTION

Technical Problem

The concentration of collagen such as fibrillar collagen in biological tissues is about 20 to 30 wt %. Accordingly, when a three-dimensional tissue is applied as a graft material, an alternative for an experimental animal, etc., it is preferable to prepare a three-dimensional tissue in which collagen is included at a concentration close to that of a biological tissue of interest.

However, previously developed three-dimensional tissue bodies are limited to those having a very high cell density due to the restriction of their production method, etc. Thus, three-dimensional tissue bodies in which the concentration of collagen is close to that of a biological tissue have previously been unknown.

The present invention has been made in light of the above situations. The purpose of the present invention is to provide a three-dimensional tissue in which the concentration of collagen is close to that of a biological tissue, a method for producing the same, and a formation agent capable of being used for production of the three-dimensional tissue.

Solution to Problem

The present inventors have conducted intensive research and, as a result, have found that the above problem can be solved by the following items of the present invention.

[1] A three-dimensional tissue comprising cells and collagen including endogenous collagen, wherein at least a portion of the cells is adhered to the collagen, and content of the collagen is from 10 wt % to 90 wt % based on the three-dimensional tissue.

[2] The three-dimensional tissue according to [1], wherein the cells comprise a collagen-producing cell.

[3] The three-dimensional tissue according to [1] or [2], wherein a residual percentage of the three-dimensional tissue after trypsin treatment at a trypsin concentration of 0.25%, a temperature of 37° C., and a pH of 7.4 for a reaction time of 15 min is 70% or more.

[4] The three-dimensional tissue according to any one of [1] to [3], wherein a thickness thereof is 10 μm or longer.

[5] The three-dimensional tissue according to any one of [1] to [4], wherein the cells comprise one or more types of cells selected from the group consisting of vascular endothelial cells, cancer cells, cardiomyocytes, smooth muscle cells, and epithelial cells.

[6] The three-dimensional tissue according to any one of [1] to [5], wherein the collagen further comprises fragmented collagen derived from exogenous collagen.

[7] A method for producing a three-dimensional tissue, comprising: step (1) of bringing cells into contact with fragmented collagen derived from exogenous collagen in an aqueous medium, and step (2) of culturing the cells brought into contact with the fragmented collagen.

[8] The method according to [7], wherein the cells are cells comprise a collagen-producing cell.

[9] The method according to [7] or [8], further comprising, between step (1) and step (2), a step of precipitating the cells and the fragmented collagen in the aqueous medium.

[10] The method according to item [7] or [8], wherein step (1) is carried out by forming a layer of the cells in the aqueous medium followed by bringing the fragmented collagen into contact with the layer.

[11] The method according to any one of [7] to [10], wherein an average length of the fragmented collagen is from 100 nm to 200 μm.

[12] The method according to any one of [7] to [11], wherein an average diameter of the fragmented collagen is from 50 nm to 30 μm.

[13] The method according to any one of [7] to [12], wherein the cells comprise one or more types of cells selected from the group consisting of vascular endothelial cells, cancer cells, cardiomyocytes, smooth muscle cells, and epithelial cells.

[14] The method according to any one of [7] to [13], wherein a mass ratio between the fragmented collagen and the cells is 900:1 to 9:1.

[15] A formation agent for a three-dimensional tissue, the agent comprising fragmented collagen, wherein an average length of the fragmented collagen is from 100 nm to 200 μm; and an average diameter of the fragmented collagen is from 50 nm to 30 μm.

Advantageous Effects of Invention

According to the present invention, there can be provided a three-dimensional tissue in which the concentration of collagen is close to that of a biological tissue, a method for producing the same, and a formation agent capable of being used for production of the three-dimensional tissue.

BRIEF DESCRIPTION OF DRAWINGS

FIGS. 6A and 6B are HE-stained and TB-stained images of each non-contractile three-dimensional tissue, including fragmented collagen and NHDFs, as produced in a well of 96-well insert (FIG. 6A) or a 24-well insert (FIG. 6B).

DESCRIPTION OF EMBODIMENTS (Three-Dimensional Tissue)

Figure 1A:
FIG. 1A is a photograph showing fragmented collagen obtained by homogenization for 2 min.

A three-dimensional tissue according to an embodiment of the present invention is a three-dimensional tissue comprising cells including a collagen-producing cell and collagen including endogenous collagen, wherein at least a portion of the cells is adhered to the collagen. In conventional three-dimensional tissue bodies, the concentration of collagen was low and the cell density was high. This has caused problems such as contraction of a three-dimensional tissue by contraction force of cells during or after culturing and rapid degradation of a three-dimensional tissue by an enzyme produced by cells during or after culturing. A three-dimensional tissue according to an embodiment is stable because the concentration of collagen is higher than that of conventional one and the contraction is thus unlikely to occur.

The "three-dimensional tissue" means a cell aggregate in which cells are three-dimensionally arranged via collagen such as fibrillar collagen, the cell aggregate being artificially made by cell culturing. Examples of the shape of the three-dimensional tissue include, but are not particularly limited to, a sheet shape, a spherical shape, an elliptical shape, and a rectangular parallelepiped shape. Examples of a biological tissue include blood vessels, sweat glands, lymphatic vessels, and sebaceous glands, and the structures of these biological tissues are more complex than the structure of a three-dimensional tissue. This makes it possible to easily distinguish between the three-dimensional tissue and a biological tissue.

Cells according to an embodiment may be cultured cells. Examples thereof include primary culture cells, subcultured cells, and cell lines.

The "collagen-producing cell" means a cell that secretes collagen such as fibrillar collagen. Examples of the collagen-producing cell include mesenchymal cells such as fibroblasts, chondrocytes, and osteoblasts. Preferred are fibroblasts. Preferable examples of the fibroblasts include human dermal fibroblasts (NHDFs), human cardiac fibroblasts (NHCFs), and human gingival fibroblasts (HGFs).

Examples of the collagen include fibrillar collagen and non-fibrillar collagen. The fibrillar collagen means collagen that is a main component of collagen fiber. Specific examples of the fibrillar collagen include type I collagen, type II collagen, and type III collagen. Examples of the non-fibrillar collagen include type IV collagen.

The "endogenous collagen" means collagen that is produced by each collagen-producing cell constituting a three-dimensional tissue. The endogenous collagen may be fibrillar collagen or non-fibrillar collagen.

The content of collagen in a three-dimensional tissue is from 0.01 to 90 wt %, preferably from 10 to 90 wt %, more preferably from 10 to 80 wt %, still more preferably from 10 to 70 wt %, still more preferably from 10 to 60 wt %, still more preferably from 1 to 50 wt %, still more preferably from 10 to 50 wt %, still more preferably from 10 to 30 wt %, and still more preferably from 20 to 30 wt %, based on the three-dimensional tissue (dry weight). As used herein, the "collagen in a three-dimensional tissue" means collagen constituting a three-dimensional tissue and may be endogenous collagen or may be exogenous collagen described later. In addition, the "collagen in a three-dimensional tissue" includes fragmented collagen described later. Specifically, when the three-dimensional tissue contains fragmented collagen derived from exogenous collagen, the concentration of collagen constituting the three-dimensional tissue means the total concentration of endogenous collagen and the fragmented collagen. The collagen concentration may be calculated from the volume of the resulting three-dimensional tissue and the mass of the decellularized three-dimensional tissue.

Examples of a method for quantifying the amount of collagen in a three-dimensional tissue include the following hydroxyproline-quantifying method. A lysate in which a three-dimensional tissue has been lysed is mixed with hydrochloric acid (HCl) and incubated at a high temperature for a predetermined time. Next, the mixture is returned to room temperature and is centrifuged. Then, the resulting supernatant is diluted at a prescribed concentration to prepare a sample. A hydroxyproline standard solution is subjected to the same treatment as above and is then serially diluted to prepare each standard. The sample and each standard are subject to given treatment using a hydroxyproline assay buffer and a detection reagent. Then, the absorbance of the sample and each standard at 570 nm is measured. The absorbance of the sample is compared to that of each standard to calculate the amount of collagen. A three-dimensional tissue may be lysed by being directly suspended in highly concentrated hydrochloric acid followed by being centrifuged to recover a supernatant, and the supernatant may be used for collagen quantification. In addition, a three-dimensional tissue collected from a culture medium may be lysed or a three-dimensional tissue collected from a culture medium may be lysed after being dried to remove a liquid component. When a three-dimensional tissue collected from a cultured medium is lysed and used to quantify collagen, it is predicted that measured values for the weight of the three-dimensional tissue may vary because the values are affected by a medium component the three-dimensional tissue absorbs and the remaining medium due to technical errors during experiment. Thus, it is preferable that the weight should be on the basis of dry weight in view of stably measuring the collagen amount per weight or unit weight of the tissue.

More specific examples include the following protocol.
(Sample Preparation)

The whole lyophilized three-dimensional tissue is mixed with 6 M HCl and is incubated in a heat block at 95° C. for 20 h or more. Then, the mixture is returned to room temperature. After the sample solution is centrifuged at 13000 g for 10 min, its supernatant is collected. The supernatant is suitably diluted with 6 M HCl such that in the measurement described later, the results are within a range of the standard curve. Then, a 200-µL aliquot is diluted with 100 µL of Milli-Q water to prepare each sample. Subsequently, 35 µL of the sample is used.
(Standard Preparation)

First, 125 µL of a standard solution (1200 µg/mL in acetic acid) and 125 µL of 12 M HCl are added to and mixed in a screw cap tube. The tube is incubated in a heat block at 95° C. for 20 h and is then returned to room temperature. After centrifuged at 13,000 g for 10 min, the supernatant is diluted with Milli-Q water to prepare S1 at 300 µg/mL. This 51 is serially diluted to prepare S2 (200 µg/mL), S3 (100 µg/mL), S4 (50 µg/mL), S5 (25 µg/mL), S6 (12.5 µg/mL), and S7 (6.25 µg/mL). S8 (0 µg/mL), which contains only 90 µL of 4 M HCl, is also prepared.
(Assay)

First, 35 µL of each standard or the sample is added to each well of a plate (coming with QuickZyme Total Collagen Assay kit; QuickZyme Biosciences, Inc.). Next, 75 µL of an assay buffer (coming with the above kit) is added to each well. The plate is sealed and is then incubated at room temperature while shaking for 20 min. Then, the seal is removed and 75 µL of a detection reagent (reagents A:B=30 µL:45 µL; coming with the above kit) is added to each well. The plate is sealed, and the resulting solution is mixed and incubated at 60° C. for 60 min while shaking. After that, the solution is cooled on ice to room temperature and the seal is removed. Finally, each absorbance at 570 nm is measured. The absorbance of the sample is compared to that of each standard to calculate the amount of collagen.

In addition, occupation of collagen in a three-dimensional tissue may be defined by the percentage of the area or volume thereof. The wording "determined by the percentage of the area or volume thereof" means that the percentage of the collagen-existing area with respect to the whole three-dimensional tissue area is calculated by macroscopic observation, various microscopy techniques, and image analysis software, etc., after collagen in a three-dimensional tissue is, for example, subject to existing staining techniques (e.g., immunostaining using an anti-collagen antibody, Masson's trichrome staining) to make the collagen distinguishable from the other tissue components. When the area percentage is used for the determination, cross-section or surface of the three-dimensional tissue used for determining the area percentage is not limited. For instance, when the three-dimensional tissue is spherical, etc., it is preferable to determine the area percentage by using a cross-sectional view, in which approximately the center portion of the three-dimensional tissue is crossed, because appearance of the whole tissue can be properly reflected.

For instance, when the amount of collagen in the three-dimensional tissue is determined by the percentage of the area thereof, the area percentage is from 0.01 to 99%, preferably from 1 to 99%, more preferably from 5 to 90%, still more preferably from 7 to 90%, still more preferably from 20 to 90%, and still more preferably from 50 to 90%, based on the whole three-dimensional tissue. The wording "collagen in a three-dimensional tissue" is as described above. When the three-dimensional tissue contains fragmented collagen derived from exogenous collagen, the percentage of the area of collagen constituting the three-dimensional tissue means the total percentage of endogenous collagen area and the fragmented collagen area. The percentage of the area of collagen may be obtained by, for instance, staining the produced three-dimensional tissue by Masson's trichrome staining and then calculating the percentage of the area of blue-stained collagen with respect to the whole cross-section in which approximately the center portion of the three-dimensional tissue is crossed.

The residual percentage of the three-dimensional tissue after trypsin treatment at a trypsin concentration of 0.25%, a temperature of 37° C. and a pH of 7.4 for a reaction time of 15 min is preferably 70% or higher, more preferably 80% or higher, and still more preferably 90% or higher. Such a three-dimensional tissue is not susceptible to enzymatic degradation during or after culturing and is thus stable. The residual percentage may be calculated from the mass of the three-dimensional tissue before and after the trypsin treatment.

The residual percentage of the three-dimensional tissue after collagenase treatment at a collagenase concentration of 0.25%, a temperature of 37° C. and a pH of 7.4 for a reaction time of 15 min is preferably 70% or higher, more preferably 80% or higher, and still more preferably 90% or higher. Such a three-dimensional tissue is not susceptible to enzymatic degradation during or after culturing and is thus stable.

The thickness of the three-dimensional tissue is preferably 10 μm or longer, more preferably 100 μm or longer, and still more preferably 1000 μm or longer. Such a three-dimensional tissue has a structure closer to the structure of a biological tissue and is suitable as graft materials and alternatives for experimental animals. The upper limit of the thickness is not particularly limited and may be, for instance, 10 mm or less, 3 mm or less, 2 mm or less, 1.5 mm or less, or 1 mm or less.

As used herein, the "thickness of a three-dimensional tissue" means the distance between both ends in a direction vertical to the main surface when the three-dimensional tissue has a sheet shape or a rectangular parallelepiped shape. If the main surface has a recess and/or a protrusion, the thickness means the distance across the thinnest portion of the main surface.

When the three-dimensional tissue is spherical, the thickness means the diameter. Furthermore, when the three-dimensional tissue is elliptical, the thickness means the short diameter. If the three-dimensional tissue is substantially spherical or substantially elliptical with a recess and/or a protrusion on the surface, the thickness means the shortest distance between two points at which the surface intersects with a line crossing the center of gravity of the three-dimensional tissue.

Cells constituting the three-dimensional tissue may further contain one or more additional cells other than a collagen-producing cell. Examples of the additional cells include vascular endothelial cells (e.g., human umbilical vein endothelial cells (HUVECs)), cancer cells such as colon cancer cells (e.g., human colon cancer cells (HT29)) and liver cancer cells, cardiomyocytes (e.g., human iPS cell-derived cardiomyocytes (iPS-CMs)), epithelial cells (e.g., human gingival epithelial cells), keratinocytes, lymphatic endothelial cells, neurons, hepatocytes, tissue stem cells, embryonic stem cells, induced pluripotent stem cells, adherent cells (e.g., immune cells), and smooth muscle cells (e.g., aortic smooth muscle cells (Aorta-SMCs)). Preferably, cells constituting the three-dimensional tissue further contain one or more types of cells selected from the group consisting of vascular endothelial cells, cancer cells, and cardiomyocytes.

The three-dimensional tissue may further contain fragmented collagen derived from exogenous collagen. The "exogenous collagen" and the "fragmented collagen" will be described below.

The three-dimensional tissue is applicable as graft materials and alternatives for experimental animals, etc.

(Method for Producing Three-Dimensional Tissue)

A method for producing a three-dimensional tissue according to an embodiment of the present invention comprises:

step (1) of bringing, in an aqueous medium, cells into contact with fragmented collagen derived from exogenous collagen; and step (2) of culturing the cells having been brought into contact with the fragmented collagen.

Cells according to an embodiment may be cultured cells. Examples include primary culture cells, subcultured cells, and cell lines. In addition, cells according to an embodiment may be cells including a collagen-producing cell, may be cells including a cell other than the collagen-producing cell, or may be cells containing both the collagen-producing cell and a cell other than the collagen-producing cell.

The "collagen-producing cell" means a cell that secretes collagen such as fibrillar collagen. Examples of the collagen-producing cell include mesenchymal cells such as fibroblasts, chondrocytes, and osteoblasts. Preferred are fibroblasts. Preferable examples of the fibroblasts include human dermal fibroblasts (NHDFs), human cardiac fibroblasts (NHCFs), and human gingival fibroblasts (HGFs).

Examples of the cell other than the collagen-producing cell include vascular endothelial cells (e.g., human umbilical vein endothelial cells (HUVECs)), cancer cells such as colon cancer cells (e.g., human colon cancer cells (HT29)) and liver cancer cells, cardiomyocytes (e.g., human iPS cell-derived cardiomyocytes (iPS-CMs)), epithelial cells (e.g., human gingival epithelial cells), keratinocytes, lymphatic endothelial cells, neurons, hepatocytes, tissue stem cells, embryonic stem cells, induced pluripotent stem cells, adherent cells (e.g., immune cells), and smooth muscle cells (e.g., aortic smooth muscle cells (Aorta-SMCs)). Preferably, cells constituting the three-dimensional tissue further include one or more types of cells selected from the group consisting of vascular endothelial cells, cancer cells, and cardiomyocytes.

A production method according to an embodiment is used to produce a stable three-dimensional tissue in which cells are uniformly distributed.

It is preferable that cells according to an embodiment comprise a collagen-producing cell. The cells comprising a collagen-producing cell can be used to produce a more stable three-dimensional tissue in which cells are uniformly distributed. The reason is postulated as follows.

In a conventional method for producing a three-dimensional tissue by using a scaffold, cells of interest are injected into a prefabricated scaffold. Thus, it has been difficult to make cells spread uniformly into the inside of the scaffold. According to a production method of an embodiment, the resulting three-dimensional tissue is stable and the cells thereof are uniformly distributed. The details of the mechanism for producing such a three-dimensional tissue are unclear but are postulated as follows. First, cells are in contact with fragmented collagen and adhere thereon. Next, the cells, by themselves, produce proteins (e.g., collagen such as fibrillar collagen) constituting an extracellular matrix (ECM). The proteins produced are in contact with the fragmented collagen and adhere thereon, so that the proteins each serve as a cross-linker between the fragmented collagen molecules. In this way, the fibrillar collagen, etc., is structured under an environment where the cells are uniformly present. This results in a more stable three-dimensional tissue in which the cells are uniformly distributed. The above postulation does not restrict the present invention.

Meanwhile, the production methods described in Patent Literatures 1 to 3 have a large number of steps for producing a three-dimensional tissue, so that about 1-h work time is needed. According to a production method of an embodiment, a three-dimensional tissue can be produced in a short work time. Further, according to a production method of an embodiment, a three-dimensional tissue can be produced easily.

In the production method described in Patent Literature 2, at least $10^6$ cells were needed to produce a three-dimensional tissue at a thickness of about 1 mm. According to a production method of an embodiment, a large-size three-dimensional tissue at a thickness of 1 mm or more can be produced by using a relatively small number of cells.

The "aqueous medium" means a liquid comprising water as an indispensable component. The aqueous medium is not particularly limited as long as fragmented collagen and cells can be present stably. Examples include saline such as phosphate buffered saline (PBS) and liquid media such as Dulbecco's Modified Eagle medium (DMEM) and vascular endothelial cell-specific medium (EGM2). The liquid medium may be a mixed medium prepared by mixing two different media. It is preferable that the aqueous medium be a liquid culture medium in view of reducing a load on cells.

The "exogenous collagen" means collagen that is externally supplied. Specific examples include fibrillar collagen and non-fibrillar collagen. An original animal species of the exogenous collagen may be the same as of endogenous collagen or may be different therefrom. Examples of the original animal species include a human, a pig, and a cow. In addition, the exogenous collagen may be synthetic collagen. It is preferable that the exogenous collagen be fibrillar collagen. Examples of the fibrillar collagen include type I collagen, type II collagen, and type III collagen. Preferred is type I collagen. Commercially available collagen may be used as the fibrillar collagen. Specific examples include lyophilized, pig skin-derived type I collagen manufactured by NH Foods Ltd. Examples of non-fibrillar exogenous collagen include type IV collagen.

An original animal species of the exogenous collagen may be different from that of the cells. When the cells include a collagen-producing cell, an original animal species of the exogenous collagen may be different from that of the collagen-producing cell. That is, the exogenous collagen may be heterologous collagen.

The "fragmented collagen" means those obtained by fragmenting collagen, such as fibrillar collagen, and having a triple helix structure. One type of collagen may be used alone to make fragmented collagen or a plurality of the types of collagen may be used in combination. Conventionally, collagen such as fibrillar collagen was dissolved in an acidic aqueous solution, etc. However, the concentration thereof was at most about 0.1 to 0.3 wt %, so that a large portion was insoluble. Accordingly, it has been difficult that conventional methods are used to increase the amount of collagen, such as fibrillar collagen, in a three-dimensional tissue. It is postulated that fragmented collagen according to an embodiment is hardly soluble in water; but when dispersed in an aqueous medium, the fragmented collagen is more easily brought into contact with the cells in the aqueous medium, thereby promoting the formation of a three-dimensional tissue. The average length of the fragmented collagen is preferably from 100 nm to 200 μm, more preferably from 22 μm to 200 μm, and still more preferably from 100 μm to 200 μm. The average diameter of the fragmented collagen is preferably from 50 nm to 30 μm, more preferably from 4 μm to 30 μm, and still more preferably from 20 μm to 30 μm.

A process for making collagen, such as fibrillar collagen, fragmented is not particularly limited. For instance, collagen such as fibrillar collagen may be fragmented by using a homogenizer such as an ultrasonic homogenizer, a stirring homogenizer, or a high-pressure homogenizer. When the stirring homogenizer is used, collagen such as fibrillar collagen may be subject to homogenization as it is or may be subject to homogenization in an aqueous medium such as saline. In addition, it is possible to prepare fragmented collagen at a millimeter or nanometer size by adjusting the time and cycle of the homogenization.

The diameter and the length of the fragmented collagen can be determined by analyzing individual fragmented collagen molecules by using an electron microscope.

A process for bringing, in an aqueous medium, cells into contact with fragmented collagen derived from exogenous collagen is not particularly limited. Examples include: a process involving adding a fragmented collagen dispersion to a culture medium containing cells; a process involving adding cells to a fragmented collagen culture medium dispersion; and a process involving adding fragmented collagen and cells to a prepared aqueous medium.

In step (1), cells including a collagen-producing cell and a cell other than the collagen-producing cell may be used. The above-described cells may be used as the collagen-producing cell or the cell other than the collagen-producing cell, respectively. Various model tissues may be constructed by producing a three-dimensional tissue by using both a collagen-producing cell and an additional cell other than the collagen-producing cell. For instance, when NHCFs and HUVECs are used, it is possible to produce a three-dimensional tissue having capillaries inside thereof. When NHCFs and colon cancer cells are used, it is possible to produce a colon cancer model tissue. Further, when NHCFs and iPS-CMs are used, it is possible to produce a cardiac muscle model tissue in which synchronous pulsations are established.

The concentration of the fragmented collagen in the aqueous medium during step (1) may be suitably determined depending on the shape and thickness of a three-dimensional tissue of interest, the size of culture-ware, etc. For instance, the concentration of the fragmented collagen in the aqueous medium during step (1) may be from 0.1 to 90 wt % or from 1 to 30 wt %.

The amount of the fragmented collagen in step (1) may be from 0.1 to 100 mg or may be from 1 to 50 mg for $1 \times 10^5$ cells.

The mass ratio between the fragmented collagen and the cells in step (1) is preferably 1000:1 to 1:1, more preferably 900:1 to 9:1, and still more preferably 500:1 to 10:1.

When both a collagen-producing cell and an additional cell are used, the (cell count) ratio of the collagen-producing cell:additional cell in step (1) may be 99:1 to 9:1, 80:20 to 50:50, 20:80 to 50:50, or 10:90 to 50:50.

The production method may further comprise, between step (1) and step (2), a step of precipitating the cells and the fragmented collagen in the aqueous medium. When such a step is carried out, the distribution of the fragmented collagen and the cells in the three-dimensional tissue becomes more uniform. The specific process is not particularly limited. Examples include a process involving centrifuging a culture medium containing the fragmented collagen and the cells.

Step (1) may be carried out by forming a layer of the cells in the aqueous medium and then bringing the fragmented collagen into contact with the layer. The layer of the cells may be formed before the contact with the fragmented collagen, so that it is possible to produce a three-dimensional tissue in which the cell density of a lower layer portion is high. In addition, the layer of the cells including a collagen-producing cell may be formed before the contact with the fragmented collagen, so that it is possible to produce a three-dimensional tissue in which the cell density of a lower layer cell portion containing the collagen-producing cell is high. Depending on the type of the cell used (e.g., an aortic smooth muscle cell), this method allows for production of a more in vivo-like tissue.

A method for producing a three-dimensional tissue according to an embodiment may comprise, after step (2), step (3) of further bringing cells into contact therewith and culturing the cells. The cells used here may be the same as the cells used in step (1) or may be different therefrom. For instance, when the cells used in step (1) include a cell other than a collagen-producing cell, the cells used in step (3) may include the collagen-producing cell. Alternatively, for example, when the cells used in step (1) include a collagen-producing cell, the cells used in step (3) may include a cell other than the collagen-producing cell. Both the cells used in step (1) and the cells used in step (3) may include a collagen-producing cell. Also, both the cells used in step (1) and the cells used in step (3) may each include a cell other than the collagen-producing cell. Step (3) may be used to produce a three-dimensional tissue with a double layer structure. For instance, when aortic smooth muscle cells and vascular endothelial cells are used as well as when human dermal fibroblasts and human epidermal keratinocytes are used, this method allows for production of a more in vivo-like tissue. In addition, for example, when human gingival fibroblasts and gingival epithelial cells are used, this method allows for production of a three-dimensional tissue with a double layer structure without tissue contraction or tissue division.

A process for culturing cells having been brought into contact with fragmented collagen is not particularly limited. Depending on the types of cultured cells, a suitable culture process may be implemented. For instance, the culture temperature may be from 20° C. to 40° C. or from 30° C. to 37° C. The pH of the culture medium may be from 6 to 8 or from 7.2 to 7.4. The culture period may be from 1 day to 2 weeks or from 1 week to 2 weeks.

The culture medium is not particularly limited. Depending on the types of cultured cells, a suitable culture medium may be selected. Examples of the culture medium include Eagle's MEM medium, DMEM, Modified Eagle medium (MEM), Minimum Essential medium, RPMI, and GlutaMax medium. The culture medium may be a serum-containing medium or a serum-free medium. The culture medium may be a mixed culture medium prepared by mixing two different culture media.

The cell density in the medium during step (2) may be suitably determined depending on the shape and thickness of a three-dimensional tissue of interest, the size of culture-ware, etc. For instance, the cell density in the medium during step (2) may be 1 to $10^8$ cells/ml or $10^3$ to $10^7$ cells/ml. In addition, the cell density in the medium during step (2) may be the same as the cell density in the aqueous medium during step (1).

The three-dimensional tissue has a contraction rate during culturing of preferably 20% or less, more preferably 15% or less, and still more preferably 10% or less. The contraction rate may be calculated by, for instance, the following equation. In the equation, L1 denotes the length of the longest portion of the three-dimensional tissue at day 1 of culturing; and L3 denotes the length of the corresponding portion of the three-dimensional tissue at day 3 of culturing.

$$\text{Contraction rate } (\%) = [(L1 - L3)/L1] \times 100.$$

The above-described production method may be used to produce, for example, a three-dimensional tissue comprising cells and collagen including endogenous collagen, wherein at least a portion of the cells is adhered to the collagen, and the content of the collagen is 10 wt % to 90 wt % based on the three-dimensional tissue. In addition, the collagen derived from exogenous collagen may be fragmented collagen.

(Formation Agent for Three-Dimensional Tissue)

A formation agent for a three-dimensional tissue according to an embodiment of the present invention is a fragmented collagen-containing formation agent for a three-dimensional tissue, wherein the average length of the fragmented collagen is from 100 nm to 200 μm; and the average diameter of the fragmented collagen is from 50 nm to 30 μm. Regarding the length of the fragmented collagen, the length of 95% of all the fragmented collagen may range from 100 nm to 200 μm Regarding the diameter of the fragmented collagen, the diameter of 95% of all the fragmented collagen may range from 50 nm to 30 μm.

The "formation agent for a three-dimensional tissue" means a reagent for producing a three-dimensional tissue. The formation agent for a three-dimensional tissue may be in a powdered state or in a state of dispersion in which fragmented collagen has been dispersed in an aqueous medium. Examples of how to prepare fragmented collagen and how to use the formation agent include the processes as indicated above in (Method for Producing Three-dimensional Tissue).

EXAMPLES

Example 1: Preparation of Fragmented Collagen by Using Type I Collagen

First, lyophilized, pig skin-derived type I collagen manufactured by NH Foods Ltd. was dispersed in 10× phosphate buffered saline (×10 PBS) and was subjected to homogenization using a homogenizer for 2 min to prepare fragmented collagen with a diameter of about 20 to 30 μm and a length of about 100 to 200 μm (FIG. 1A). The diameter and the length of the fragmented collagen were determined by analyzing individual fragmented collagen molecules by using an electron microscope. The resulting fragmented collagen was washed with a serum-free medium (DMEM) to prepare a fragmented collagen culture medium dispersion. The prepared fragmented collagen culture medium dispersion was successfully stored at room temperature for 1 week. In the production of each three-dimensional tissue described later, the fragmented collagen as obtained by substantially the same process was used.

Figure 1B:
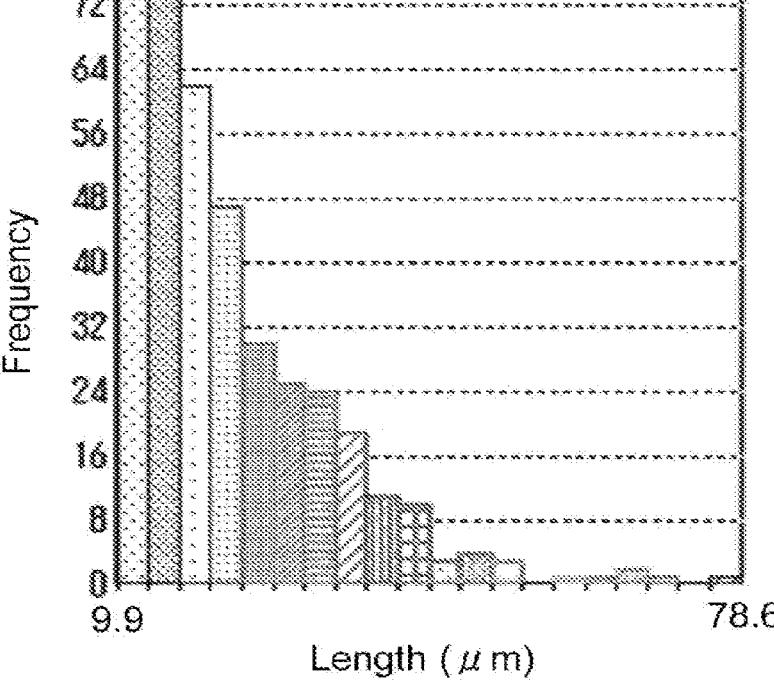
FIG. 1B is a histogram showing a length distribution of fragmented collagen obtained by homogenization for 5 min.

In addition, when the homogenization time was changed to 5 min in the above process, fragmented collagen with a diameter of about 950 nm to 16.8 μm and a length of about 9.9 μm to 78.6 μm was obtained (Table 1, FIG. 1B). The results have revealed that by adjusting the homogenization time, the size of fragmented collagen can be controlled.

TABLE 1

| Size of fragmented collagen after 5-min homogenization (the number of samples: 391) | | |
|---|---|---|
| | Length (μm) | Diameter (μm) |
| Minimum | 9.9 | 0.95 |
| Maximum | 78.6 | 16.8 |
| Average | 22.5 | 4.4 |
| Standard deviation | 11.0 | 2.6 |

Figure 2A:
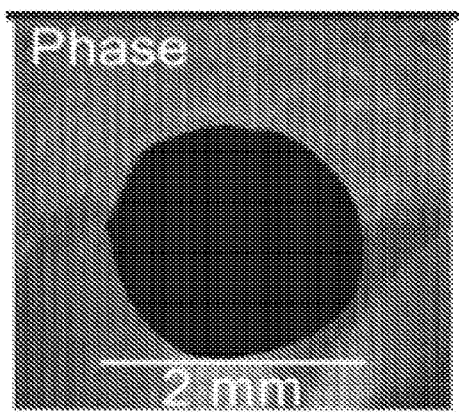
FIG. 2A is a phase contrast microscope image.
Figure 2B:
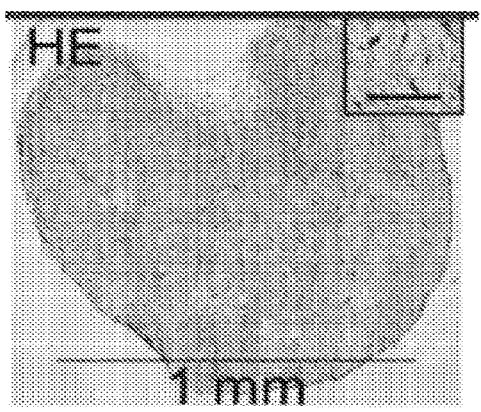
FIG. 2B is a hematoxylin-eosin (HE)-stained image.
Figure 2C:
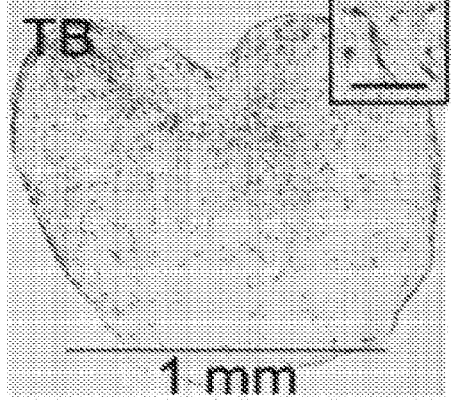
FIG. 2C is a toluidine blue (TB)-stained image of a three-dimensional tissue including fragmented collagen and normal human dermal fibroblasts (NHDFs) after one-week of culturing.

Example 2: Production of Three-Dimensional Tissue by Using Human Dermal Fibroblasts Fragmented collagen was dispersed at a concentration of 6.02 mg/ml in a serum-containing medium (DMEM). As the fragmented collagen was used those prepared by homogenization for 2 min in Example 1. Next, 166 μl of the resulting dispersion (equivalent to about 1 mg of fragmented collagen) and $1 \times 10^5$ normal human dermal fibroblasts (NHDFs) were added to a non-adherent 96-well round-bottom plate. As the culturing started, a mixture containing the cells and the fragmented collagen became a round shape. After 1 week of culturing, a spherical three-dimensional tissue with a diameter of about 1.5 mm was produced (FIG. 2A). The resulting three-dimensional tissue was subjected to hematoxylin-eosin (HE) staining or toluidine blue (TB) staining. The staining revealed that the fragmented collagen and the NHDFs were each uniformly distributed (FIGS. 2B and 2C). The calculated collagen content of the resulting three-dimensional tissue was about 30 wt %.

Figure 3:
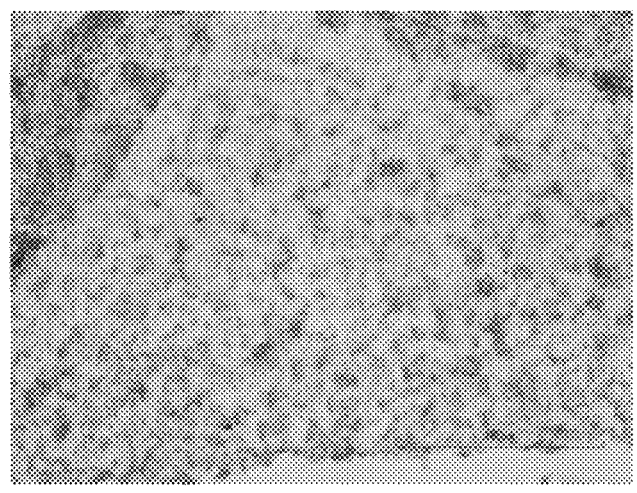
FIG. 3 is a photograph of a three-dimensional tissue, including fragmented collagen and NHDFs, immunostained by using an anti-human collagen antibody.

The NHDFs used were originated from a human. Accordingly, when immunostaining is performed using an anti-human collagen antibody, it is possible to stain and distinguish between human collagen produced by the cells and the fragmented collagen derived from pig type I collagen (fragmented collagen derived from exogenous collagen). The preliminary results demonstrated, in the inside of the three-dimensional tissue, staining of human collagen (endogenous collagen) derived from the NHDFs (FIG. 3). The results have revealed that when endogenous collagen and exogenous collagen are derived from different species, the endogenous collagen and fragmented collagen derived from the exogenous collagen in the three-dimensional tissue are distinguishable.

Figure 4A:
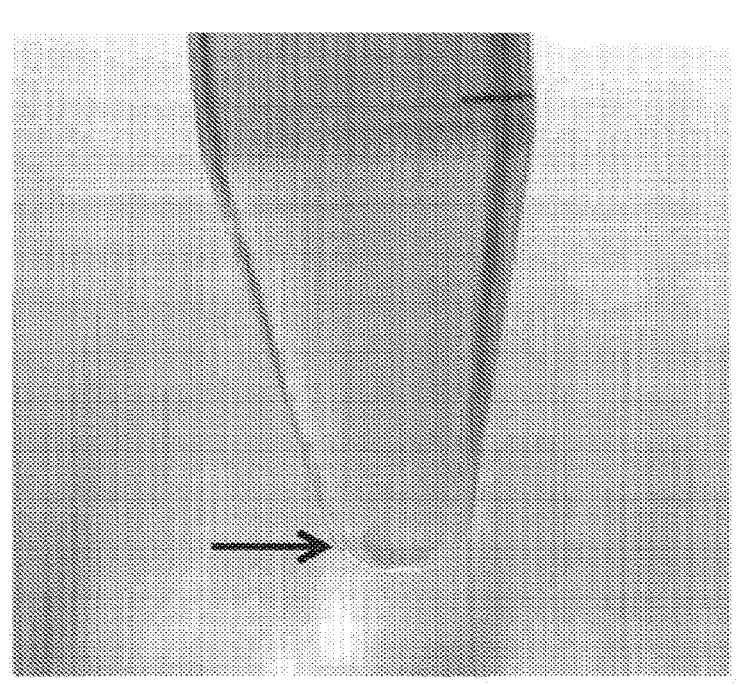
FIGS. 4A and 4B are photographs showing how a three-dimensional tissue including fragmented collagen and NHDFs looks like before (FIG. 4A) and after (FIG. 4B) trypsin treatment.
Figure 4B:
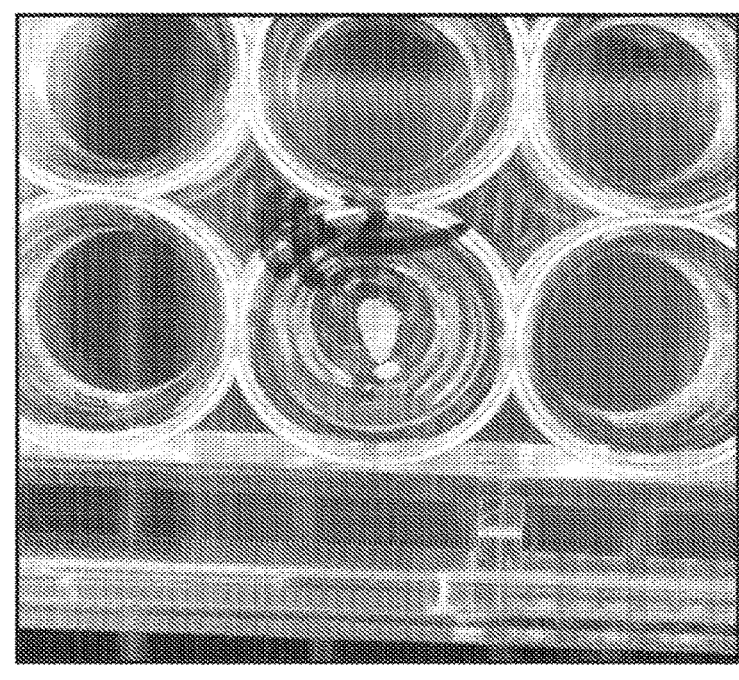

The resulting three-dimensional tissue was subjected to trypsin treatment at a trypsin concentration of 0.25%, a temperature of 37° C., and a pH of 7.4 for a reaction time of 15 min. Then, almost no trypsin-mediated disintegration was observed (FIG. 4, the residual percentage of 90%). The results have suggested that the produced three-dimensional tissue is stable when treated with an enzyme such as trypsin.

Figures 5A, 5B:
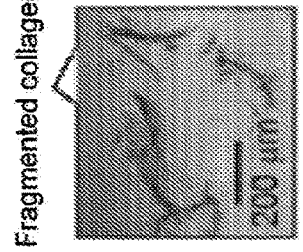
FIG. 5A is a diagram schematically illustrating a step of producing a three-dimensional tissue including fragmented collagen, NHDFs, and human umbilical vein endothelial cells (HUVECs).
FIG. 5B is a photograph of a three-dimensional tissue immunostained by using an anti-CD31 antibody.

Example 3: Production of Three-Dimensional Tissue by Using Human Dermal Fibroblasts and Human Umbilical Vein Endothelial Cells NHDFs and human umbilical vein endothelial cells (HU-VECs) were mixed at a 80:20 ratio (the number of cells) and seeded on a non-adherent 96-well round-bottom plate. At this time, fragmented collagen prepared by homogenization for 2 min in Example 1 was used and added in an amount designated in Example 2 while the total number ($1.0 \times 10^5$ cells) of the cells seeded was used as a reference. After that, the mixture was cultured for 1 week in a 1:1 (volume ratio) mixed medium of DMEM and vascular endothelial cell-specific medium (EGM2; manufactured by LONZA, Inc.) to produce a three-dimensional tissue (FIG. 5A). The calculated collagen content of the resulting three-dimensional tissue was about 30 wt %. When the produced three-dimensional tissue was stained with an anti-CD31 antibody, even the inside of the three-dimensional tissue was found to be stained (FIG. 5B). The results have demonstrated that a three-dimensional tissue containing capillaries can be produced.

Example 4: Production of Non-Contractile Three-Dimensional Tissue by Using Human Dermal Fibroblasts First, 10 mg of fragmented collagen (those prepared by homogenization for 2 min in Example 1) and $10 \times 10^5$ NHDFs were mixed and the mixture was seeded and cultured on each of adherent 96-well and 24-well inserts. Then, three-dimensional tissue bodies with a thickness of about 3 mm or 1 mm were produced and almost no contraction of each three-dimensional tissue was observed (FIG. 6). The calculated collagen content of the three-dimensional tissue produced in the 96-well insert was about 30 wt %. The calculated collagen content of the resulting three-dimensional tissue produced in the 24-well insert was about 30 wt %.

Figure 7A:
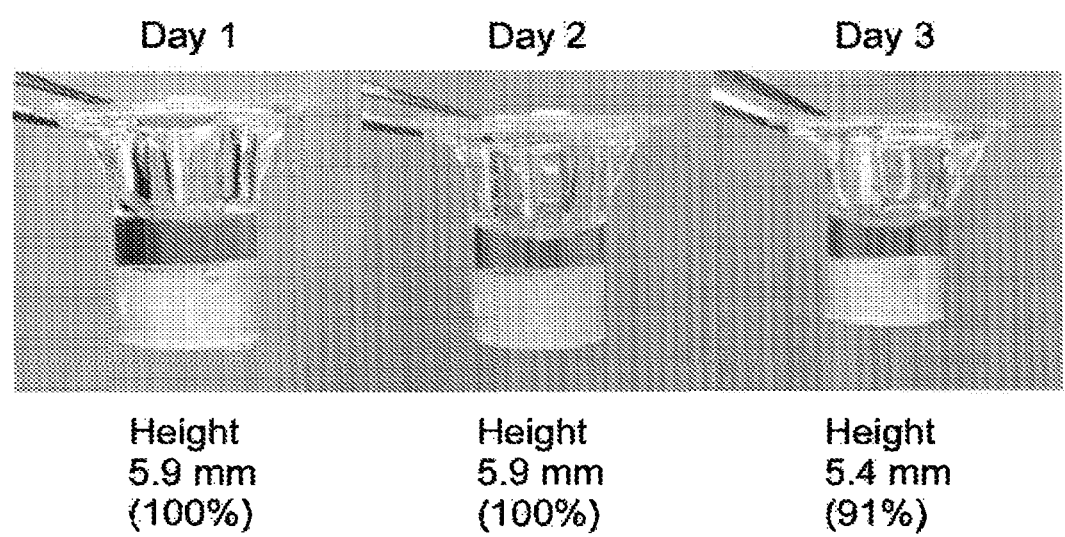
FIGS. 7A and 7B are photographs showing the observation of how a three-dimensional tissue (FIG. 7A) including fragmented collagen-containing collagen gel and NHDFs or a three-dimensional tissue (FIG. 7B) including collagen gel and NHDFs was contracted during culturing.
Figure 7B:
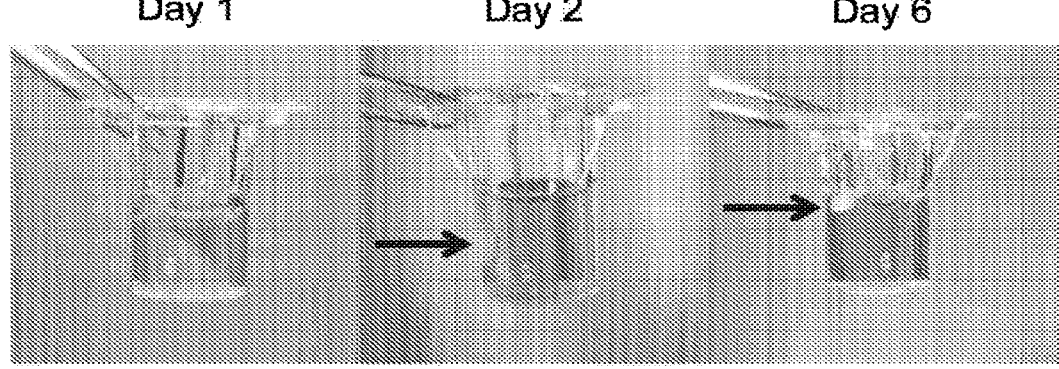

In addition, 100 μl of collagen gel containing 30 mg of the fragmented collagen and $10 \times 10^5$ NHDFs were mixed and the mixture was seeded and cultured on an adherent 24-well insert. Then, almost no contraction of the resulting three-dimensional tissue was observed (FIG. 7A). By contrast, when fragmented collagen-free collagen gel (at a collagen concentration of 0.3 wt %) was used to produce a three-dimensional tissue, its contraction was observed at day 2 of culturing and it was observed that the three-dimensional tissue became spherical at day 6 of culturing (FIG. 7B).

Figure 8:
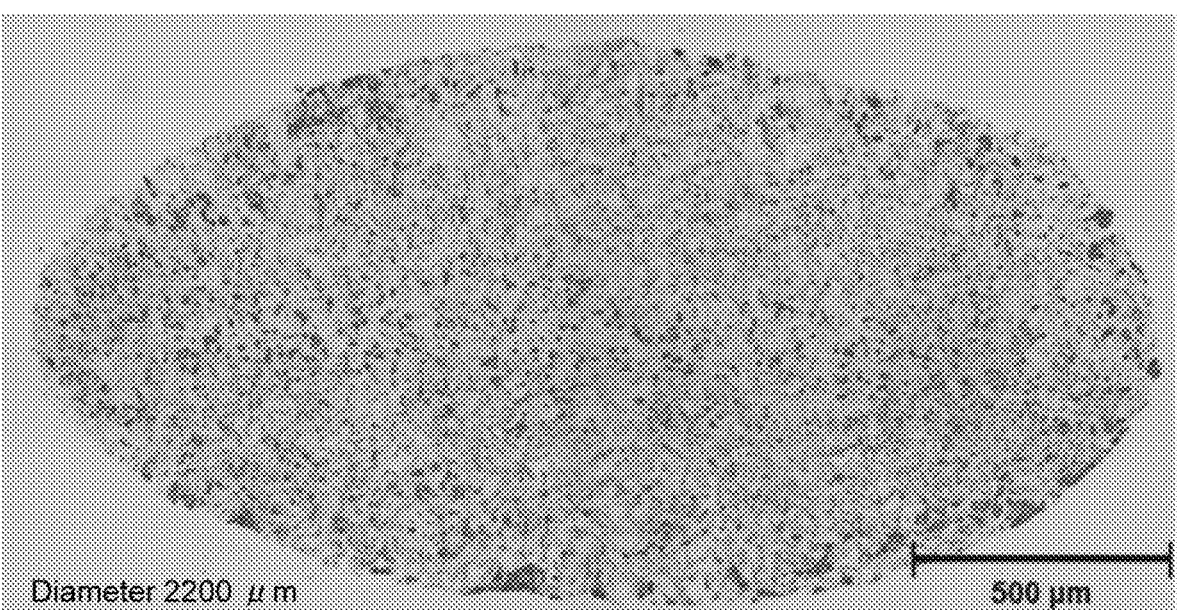
FIG. 8 is an HE-stained image of a three-dimensional tissue including fragmented collagen, NHDFs, and human colon cancer cells (HT29).

Example 5: Production of Three-Dimensional Tissue by Using Human Dermal Fibroblasts and Human Colon Cancer Cells A three-dimensional tissue was successfully produced by mixing NHDFs and cancer cells. Specifically, the same conditions as of Example 2 were used to produce a three-dimensional tissue, except that human colon cancer cells HT29 and NHDFs were mixed at a 1:1 ratio (the total number of cells: $1.0 \times 10^5$ cells) and seeded on a non-adherent 96-well round-bottom plate. An HE-stained image of the resulting three-dimensional tissue was shown in FIG. 8. It was observed that HT29 and NHDFs were uniformly distributed in the inside of the three-dimensional tissue with a diameter of about 2 mm. The calculated collagen content of the three-dimensional tissue produced was about 30 wt %.

Figure 9:
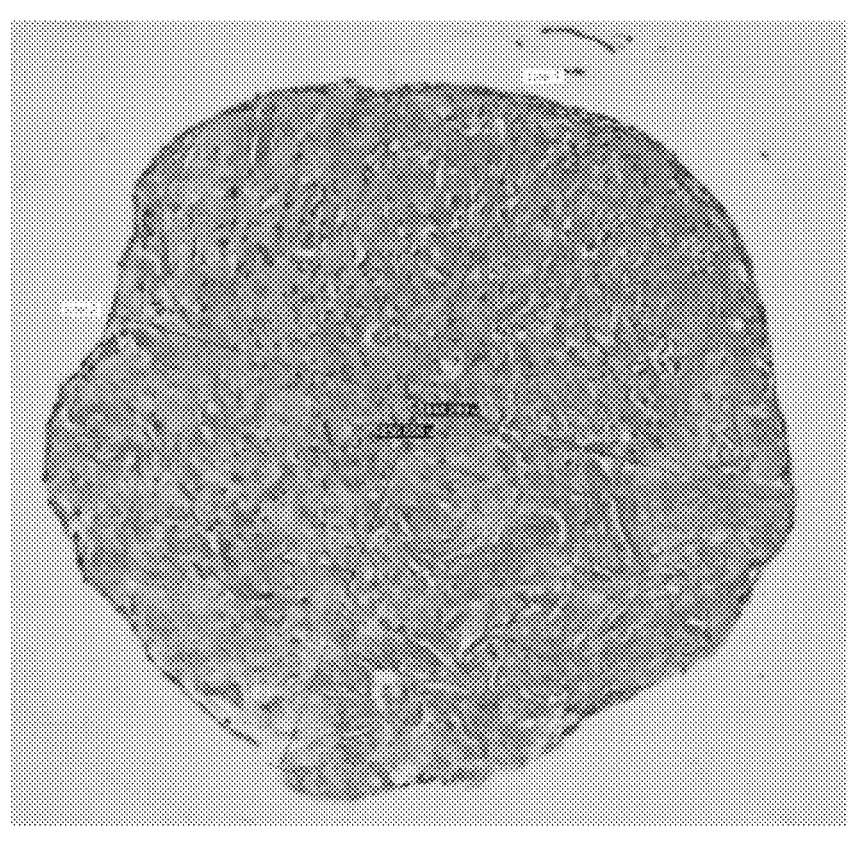
FIG. 9 is an HE-stained image of a three-dimensional tissue including fragmented collagen, human cardiac fibroblasts (NHCFs), and iPS cell-derived cardiomyocytes (iPS-CMs).

Example 6: Production of Three-Dimensional Tissue by Using Human Cardiac Fibroblasts and Human iPS Cell-Derived Cardiomyocytes In substantially the same procedure, a three-dimensional tissue was produced by using human cardiac fibroblasts (NHCFs) and human iPS cell-derived cardiomyocytes (iPS-CMs) (FIG. 9). Specifically, the same conditions (the total number of cells was $1.0 \times 10^5$ cells) as of Example 2 were used to produce a three-dimensional tissue, except that the NHCFs and the iPS-CMs were mixed at a 25:75 ratio and seeded on a non-adherent 96-well round-bottom plate. The calculated collagen content of the three-dimensional tissue produced was about 30 wt %. The produced three-dimensional tissue exhibited a synchronous pulsation about 30 to 40 times per min even after 1 to 2 weeks of culturing. The experimental results have suggested that the iPS-CMs in the three-dimensional tissue are under an environment close to that of in vivo cardiomyocytes. In addition, it has been suggested that the three-dimensional tissue according to the present invention is a tissue suitable as graft materials and alternatives for experimental animals.

Figure 10:
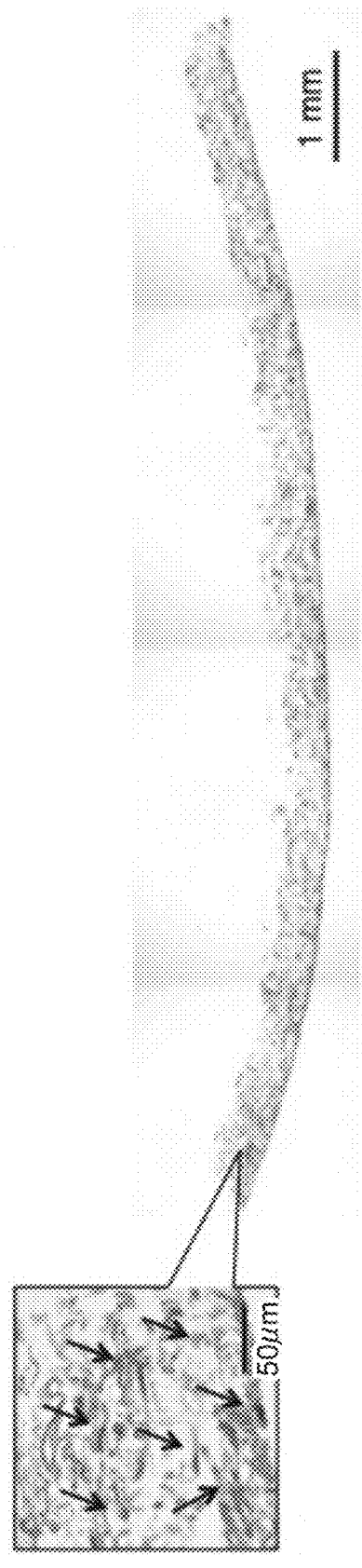
FIG. 10 is an HE-stained image of a three-dimensional tissue, including fragmented collagen and human aortic smooth muscle cells (Aorta-SMCs), as obtained by a method in which the cells and the fragmented collagen are added at the same time. Each arrow shows an exemplary location where the Aorta-SMC is present.

Example 7: Production of Three-Dimensional Tissue by Using Human Aortic Smooth Muscle Cells First, lyophilized, pig skin-derived type I collagen manufactured by NH Foods Ltd. was dispersed in 10× phosphate buffered saline (×10 PBS) and was subjected to homogenization using a homogenizer for 2 min to prepare fragmented collagen. The fragmented collagen was dispersed at a concentration of 10 mg/ml in a serum-containing medium (SmGM-2, manufactured by LONZA, Inc.). Next, 200 μl of the resulting dispersion (equivalent to about 2 mg of fragmented collagen) and $1 \times 10^5$ normal human aortic smooth muscle cells (Aorta-SMCs) were added to a 24-well cell culture insert (manufactured by Corning, Inc.). As the culturing started, a mixture containing the cells and the fragmented collagen became a shape fit for the insert. After 1 week of culturing, a three-dimensional tissue with a thickness of about 0.3 mm was produced. The resulting three-dimensional tissue was fixed with 10% paraformaldehyde (PFA) and stained with hematoxylin-eosin (HE). The staining revealed that the fragmented collagen and the Aorta-SMCs were each uniformly distributed (FIG. 10). Although the thickness varied, substantially the same results were obtained in the cases of using about 3 mg, 4 mg, or 8 mg of the fragmented collagen.

Figure 11:
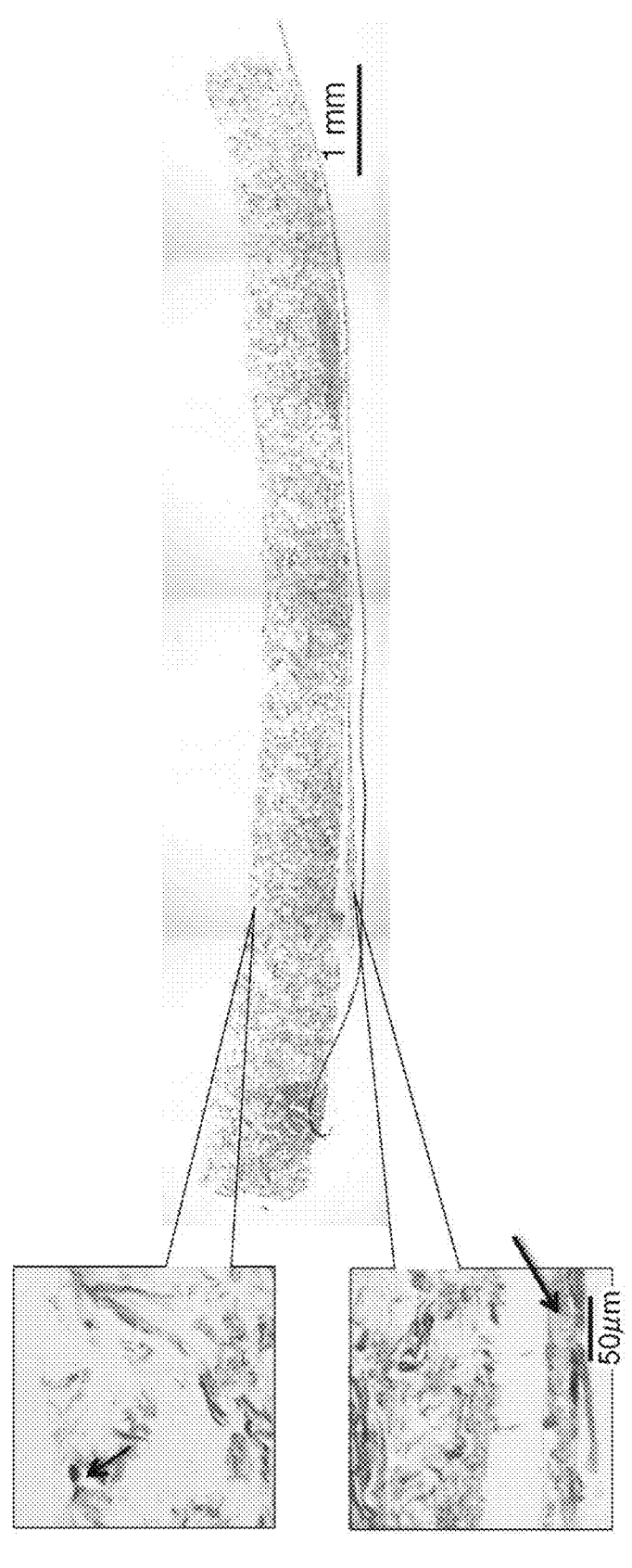
FIG. 11 is an HE-stained image of a three-dimensional tissue, including fragmented collagen and human aortic smooth muscle cells (Aorta-SMCs), as produced by a Bottom Layer Method. Each arrow shows an exemplary location where the Aorta-SMC is present.

A three-dimensional tissue was produced by a method (Bottom Layer Method) including forming an Aorta-SMC layer and then causing fragmented collagen to contact the layer by using the same fragmented collagen dispersion and Aorta SMCs as described above. Next, 200 μl of SmGM-2 (manufactured by LONZA, Inc.) and $2.5 \times 10^4$ SMCs were added to a 24-well cell culture insert (manufactured by Corning, Inc.). After 24 h of culturing, the Aorta-SMCs adhered on the bottom surface of the insert to form a cell layer. Then, 400 μl of the fragmented collagen dispersion (equivalent to about 8 mg of fragmented collagen) was added onto the Aorta-SMC layer. After 1 week of culturing, a three-dimensional tissue with a thickness of about 0.8 mm was produced. The resulting three-dimensional tissue was fixed with 10% paraformaldehyde (PFA) and stained with hematoxylin-eosin (HE). The staining revealed that the SMCs were distributed mainly in a lower layer portion and a more in vivo-like tissue was formed (FIG. 11).

The three-dimensional tissue as obtained by the method including adding fragmented collagen and Aorta-SMCs at the same time was compared with the three-dimensional tissue as obtained by the Bottom Layer Method. Then, no difference in the thickness between both the three-dimensional tissue bodies was observed. In the both methods, the thickness tended to increase depending on the number of Aorta-SMCs used. In the three-dimensional tissue obtained by the former method, no significant difference in the density between a lower layer portion and an upper layer portion was observed. By contrast, in the three-dimensional tissue obtained by the latter method, there was a tendency that the cell density of a lower layer portion was high and the cell density of an upper layer portion was low. This three-dimensional tissue was found to be a structure closer to an in vivo aortic smooth muscle tissue.

Figure 12:
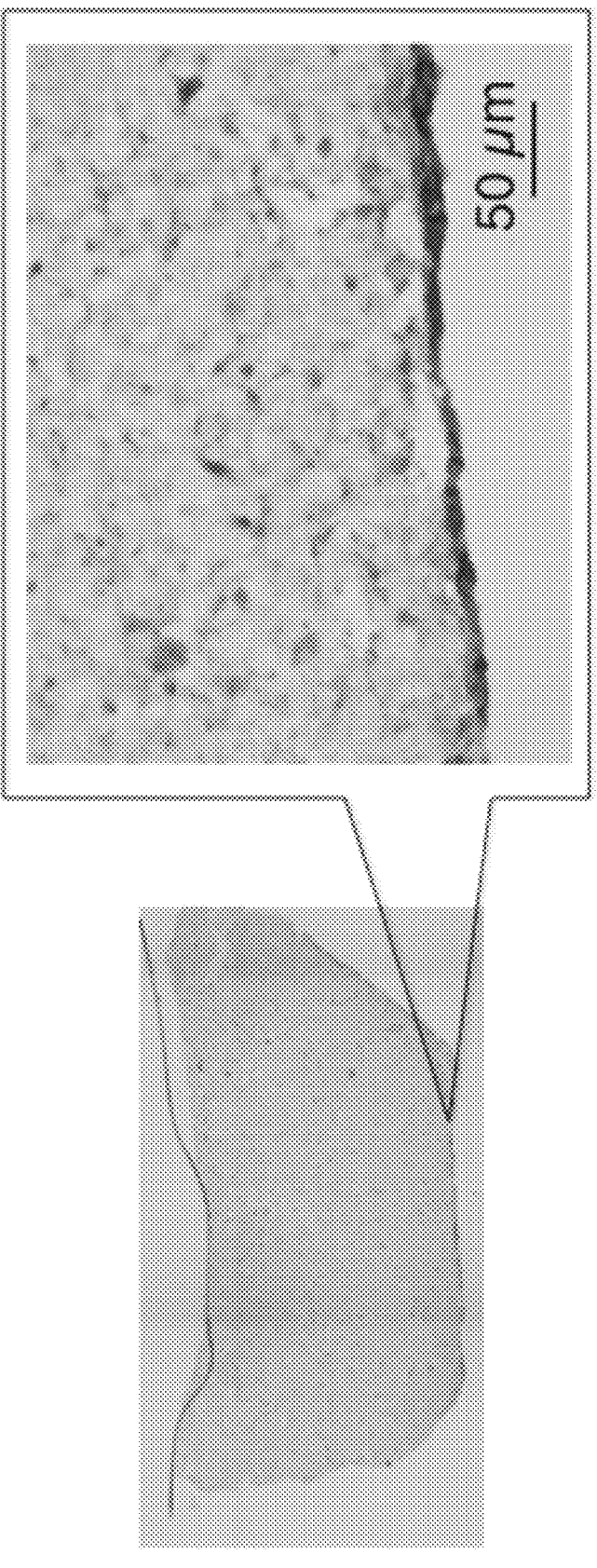
FIG. 12 is photographs of a double-layer-structure three-dimensional tissue, including fragmented collagen, human aortic smooth muscle cells (Aorta-SMCs), and human umbilical vein endothelial cells (HUVECs), immunostained by using an anti-CD31 antibody. The black layer at a bottom portion in the magnified image is a HUVEC layer.

Example 8: Production of Three-Dimensional Tissue with Double Layer Structure by Using Human Aortic Smooth Muscle Cells and Human Umbilical Vein Endothelial Cells Like Example 7, 200 μl of a dispersion prepared by suspending fragmented collagen in a culture medium (equivalent to about 3 mg of fragmented collagen) and $5.0 \times 10^5$ Aorta-SMCs were suspended and added to a 96-well insert (manufactured by ACEA Bioscience, Inc.). The mixture was then cultured for 1 week to construct a three-dimensional tissue. Further, $6 \times 10^4$ human umbilical vein endothelial cells (HUVECs) were suspended in a culture medium, naturally sedimented, and deposited on the three-dimensional tissue constructed. The resulting three-dimensional tissue was fixed with 10% PFA, sectioned, and CD31-immunostained. After 24 h of culturing, an endothelial cell monolayer was constructed on the three-dimensional tissue, so that a tissue closer to an in vivo blood vessel wall was produced (FIG. 12).

Figure 13:
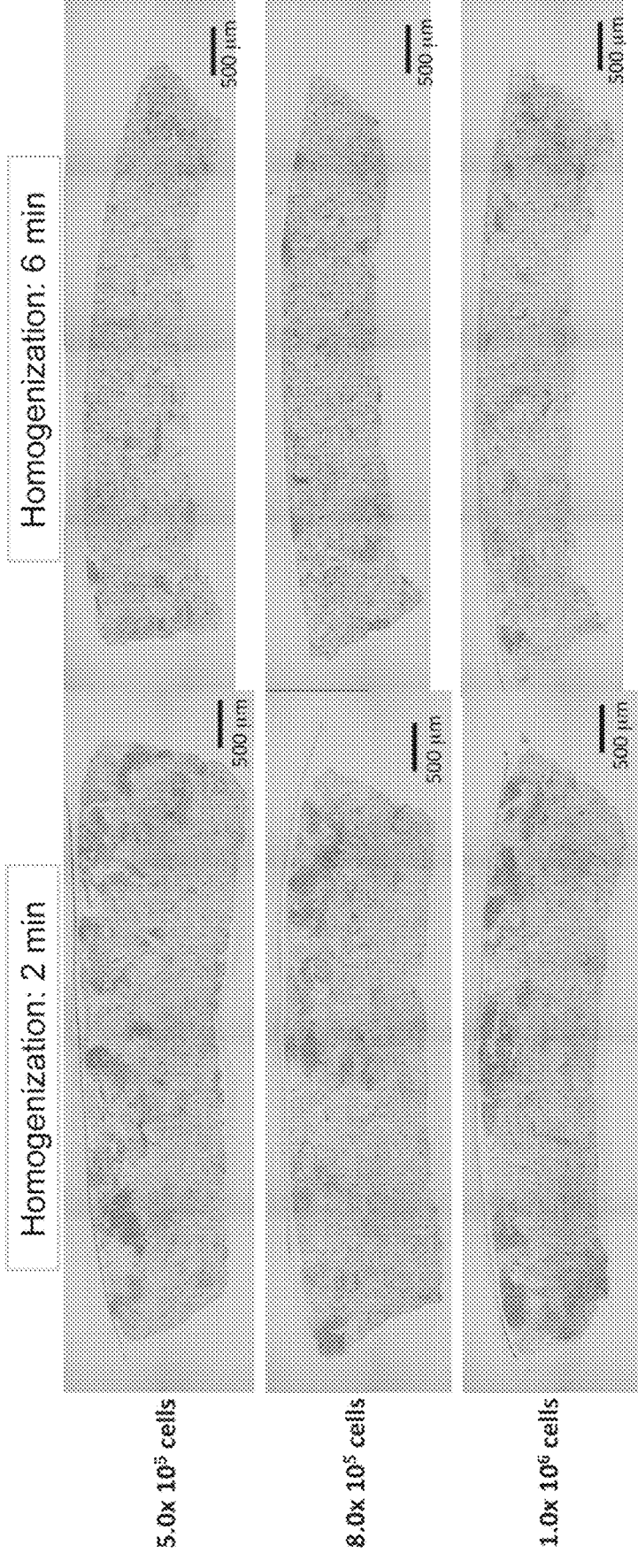
FIG. 13 is HE-stained images of three-dimensional tissue bodies including fragmented collagen and human gingival fibroblasts (HGFs). The left panels show the results of using fragmented collagen obtained by homogenization for 2 min; and the right panels show the results of using fragmented collagen obtained by homogenization for 6 min.

Example 9: Production of Three-Dimensional Tissue by Using Human Gingival Fibroblasts First, lyophilized, pig skin-derived type I collagen manufactured by NH Foods Ltd. was dispersed in 10× phosphate buffered saline (×10 PBS) and was subjected to homogenization using a homogenizer for 2 min to prepare fragmented collagen. The fragmented collagen was dispersed at a concentration of 10 mg/ml in a serum-containing medium (DMEM). Next, 800 μl of the dispersion (equivalent to about 8 mg of fragmented collagen) obtained (at the time of 2-min homogenization) and normal human gingival fibroblasts (HGFs) ($5.0 \times 10^5$ cells, $8.0 \times 10^5$ cells, or $1.0 \times 10^6$ cells) were added to a 24-well cell culture insert (manufactured by Corning, Inc.). As the culturing started, a mixture containing the cells and the fragmented collagen became a cylindrical fit for the insert shape. Day 3 after culturing, a three-dimensional tissue with a thickness of about 1.5-mm diameter was produced. Although a large amount of collagen was present, a tissue contraction was hardly seen. The resulting three-dimensional tissue was stained by hematoxylin-eosin (HE). The results demonstrated that in each three-dimensional tissue using each of $5.0 \times 10^5$ cells, $8.0 \times 10^5$ cells, or $1.0 \times 10^6$ cells of HGFs, the fragmented collagen and the HGFs were each uniformly distributed (FIG. 13 "Homogenization: 2 min").

The same protocol was repeated to produce another three-dimensional tissue, except that fragmented collagen prepared by homogenization using a homogenizer for 6 min was used. Each three-dimensional tissue was produced by using 816 μl of the dispersion (equivalent to about 8 mg of fragmented collagen) and each of $5.0 \times 10^5$ cells, $8.0 \times 10^5$ cells, or $1.0 \times 10^6$ cells of HGFs. The results revealed that the fragmented collagen and the HGFs were each uniformly distributed (FIG. 13 "Homogenization: 6 min").

The three-dimensional tissue produced using the fragmented collagen prepared by 2-min homogenization was compared with the three-dimensional tissue produced using the fragmented collagen prepared by 6-min homogenization. In the both cases, each three-dimensional tissue was obtained in which the fragmented collagen and the HGFs were each uniformly distributed. However, the three-dimensional tissue produced using the fragmented collagen prepared by 6-min homogenization had a smaller number of collagen aggregates and was thus more uniform. The thickness is thinner when the same amount of collagen was used.

Example 10: Production of Three-Dimensional Tissue by Using Human Gingival Fibroblasts and Gingival Epithelial Cells Lower Layer (HGF Layer) Construction: 8 mg of pig skin-derived type I collagen (fragmented by 2-min homogenization) manufactured by NH Foods Ltd. and $1.0 \times 10^6$ normal human gingival fibroblasts (HGFs) were mixed and suspended in D-MEM (manufactured by Wako Pure Chemical Industries, Ltd.); the mixture was added to a 24-well insert (manufactured by Corning, Inc.); a culture medium was added to the outside of the insert; and the mixture was then cultured overnight.

Upper Layer (Epi4 Layer) Construction: next day, the culture medium of the insert was aspirated; immortalized human gingival epithelial cells (Epi4) were adjusted at $2.0 \times 10^6$ cells/300 μl/insert and the Epi4 cells were seeded on the HGF layer. Next, 1 ml of a 1:1 mixture of D-MEM and Humedia (manufactured by KURABO INDUSTRIES LTD.) was placed outside the insert and incubated at 37° C. for 1 h. Then, 1 ml of the mixed medium was added to the outside of the insert and the cells were cultured overnight.

Epi4 Differentiation: the media placed both inside and outside the insert were removed; the mixed medium was added to the outside of the insert; and the cells were cultured while the medium was changed every day for 7 days. After the culturing, the resulting tissue was sectioned and HE-stained.

The above protocol was repeated to produce another three-dimensional tissue, except that pig skin-derived type I collagen, manufactured by NH Foods Ltd., fragmented by 6-min homogenization was used during the lower layer construction. Then, the resulting three-dimensional tissue was HE-stained.

Figure 14:
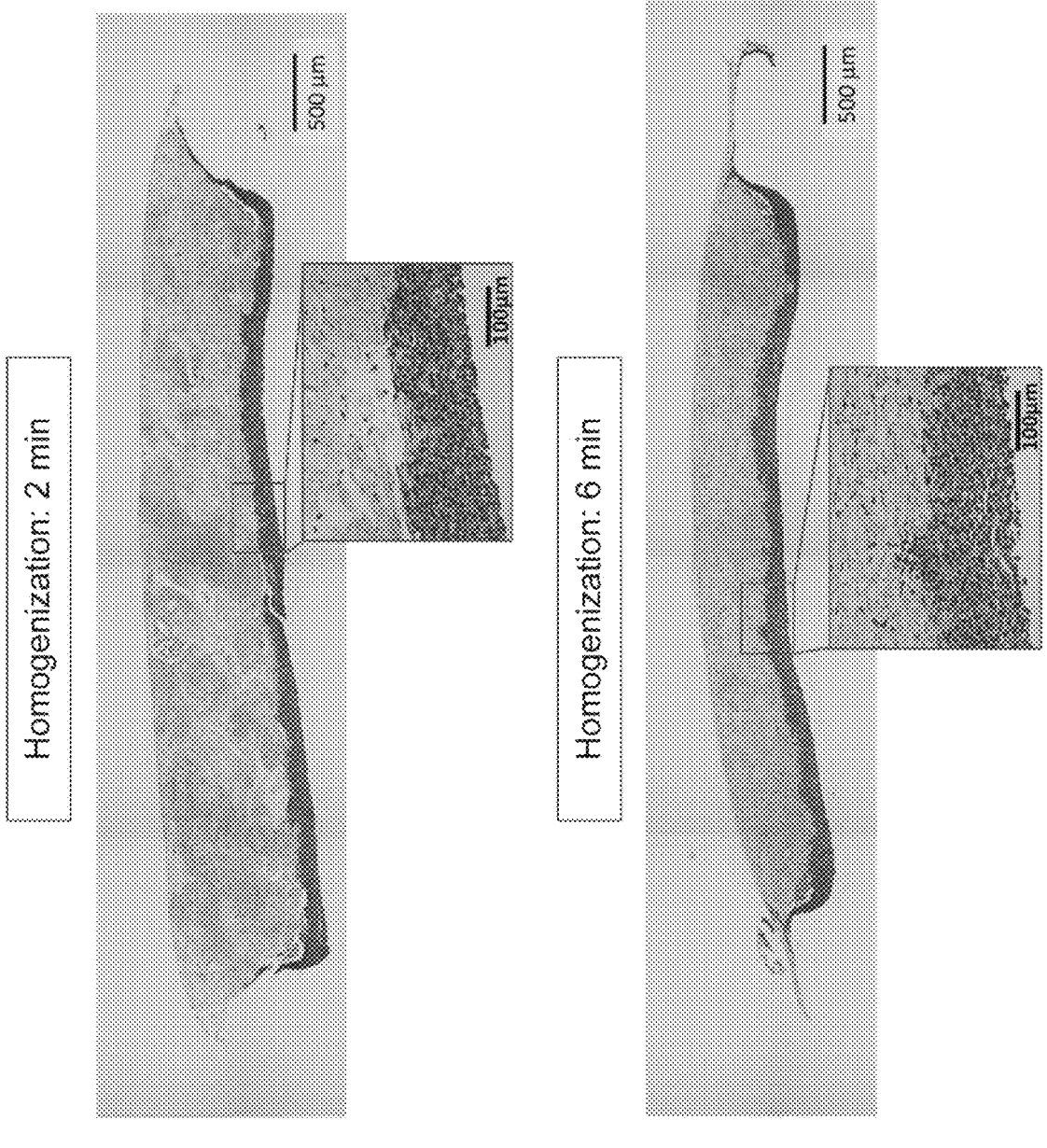
FIG. 14 is HE-stained images of three-dimensional tissue bodies including fragmented collagen, human gingival fibroblasts (HGFs), and immortalized human gingival epithelial cells (Epi4). The upper panels show the results of using fragmented collagen obtained by homogenization for 2 min; and the lower panels show the results of using fragmented collagen obtained by homogenization for 6 min.

As shown in FIG. 14, a stromal foundation was constructed using fragmented collagen prepared by 2-min homogenization or fragmented collagen prepared by 6-min homogenization; and gingival epithelial cells were layered thereon. This made it possible to produce a gingival model with a double layer structure without tissue contraction or tissue division.

Example 11: Production of Three-Dimensional Tissue with Double Layer Structure by Using Human Dermal Fibroblasts and Normal Human Epidermal Keratinocytes First, 50 mg of lyophilized, pig skin-derived type I collagen manufactured by NH Foods Ltd. was dispersed in 5 mL of 10× phosphate buffered saline (×10 PBS) and was subjected to homogenization using a homogenizer for 2 min to prepare fragmented collagen. The resulting fragmented collagen was washed with a serum-free medium (DMEM) to prepare a fragmented collagen culture medium dispersion. The fragmented collagen was dispersed at a concentration of 10 mg/ml in a serum-containing medium (SmGM-2; manufactured by LONZA, Inc.).

Lower Layer (NHDF layer) Construction: a 24-well insert was coated with 0.04 mg/mL fibronectin solution (#F2006-5G manufactured by Sigma, Inc.) in PBS (0.04 μL/insert) and was incubated at 37° C. for 20 min Next, 0.8 mL of the fragmented collagen dispersion (equivalent to about 8 mg of fragmented collagen) and $1 \times 10^6$ human dermal fibroblasts (NHDF) were mixed in a 24-well plate transwell (manufactured by IWAKI, Inc.). The plate was placed in an incubator and the cells were cultured for 24 h.

Upper Layer (NHEK) Construction: the culture medium inside the insert was aspirated on collagen gel having the NHDFs; 0.04 mg/mL collagen IV solution in PBS (0.04 μL/insert) was used for coating; and the resulting materials were incubated at 37° C. for at least 20 min. The collagen IV solution added to the collagen gel having the NHDFs was aspirated. Next, 300 μL of $1 \times 10^6$ normal human epidermal keratinocytes (NHEKs) (#KK-4009; 1 vial=500000 cells; manufactured by KURABO INDUSTRIES LTD.) were added onto the collagen gel having the NHDFs. Then, 1 mL of a 5% FBS-containing DMEM:EpiLife (#C-2517A; manufactured by Invitrogen, Inc.) (1:1) medium was added to the outside of the insert. After 1 hour, another 1 mL was added to the outside of the insert.

The inside and outside media were gently aspirated. Ascorbic acid was diluted 100-fold in the 5% FBS-containing DMEM:EpiLife (1:1) medium and was then added to the outside of the insert as 500 μL of a differentiation medium. No culture medium was added to the inside of the insert. Up to day 7 of differentiation, the medium outside the insert was changed every day.

The constructed skin model had a proper distance between cells in the fibroblast-containing layer (dermal tissue) and the upper keratinocyte-containing layer (epidermal tissue), and had a structure close to an in vivo skin tissue. The fragmented collagen prepared by 2-min homogenization and the human dermal fibroblasts were used to construct a foundation; and the normal human epidermal keratinocytes were layered thereon. This made it possible to construct an in vivo-like double layer-structure skin model.

Example 12: Production of Three-Dimensional Tissue by Using Human Cardiac Fibroblasts and Human iPS Cell-Derived Cardiomyocytes and Calculation of Percentage of Collagen Area First, 50 mg of lyophilized, pig skin-derived type I collagen manufactured by NH Foods Ltd. was dispersed in 5 mL of 10× phosphate buffered saline (×10 PBS) and was subjected to homogenization using a homogenizer for 6 min to prepare fragmented collagen (CMF). After centrifugation at 3500 rpm for 3 min, a serum-free medium (DMEM) was added. The mixture was washed for 1 min and centrifuged again at 3500 rpm for 3 min to remove the supernatant. A serum-containing medium (DMEM) was then added at a total volume of 5 ml and the fragmented collagen was dispersed.

Next, $5\times10^5$ cells containing human cardiac fibroblasts (NHCFs) and human iPS cell-derived cardiomyocytes (iPS-CMs) at a 25:75 ratio and the CMF at 0, 0.1, 0.5, 1.0, 1.5, or 2.0 mg were mixed at a total liquid volume of 300 µL and were seeded onto a non-adherent 96-well round-bottom plate (the concentration of the solution was calculated as 6.5 mg/mL). After centrifugation at 1100 g for 5 min, the mixture was cultured in an incubator for 21 days to produce each three-dimensional tissue.

Figure 15:
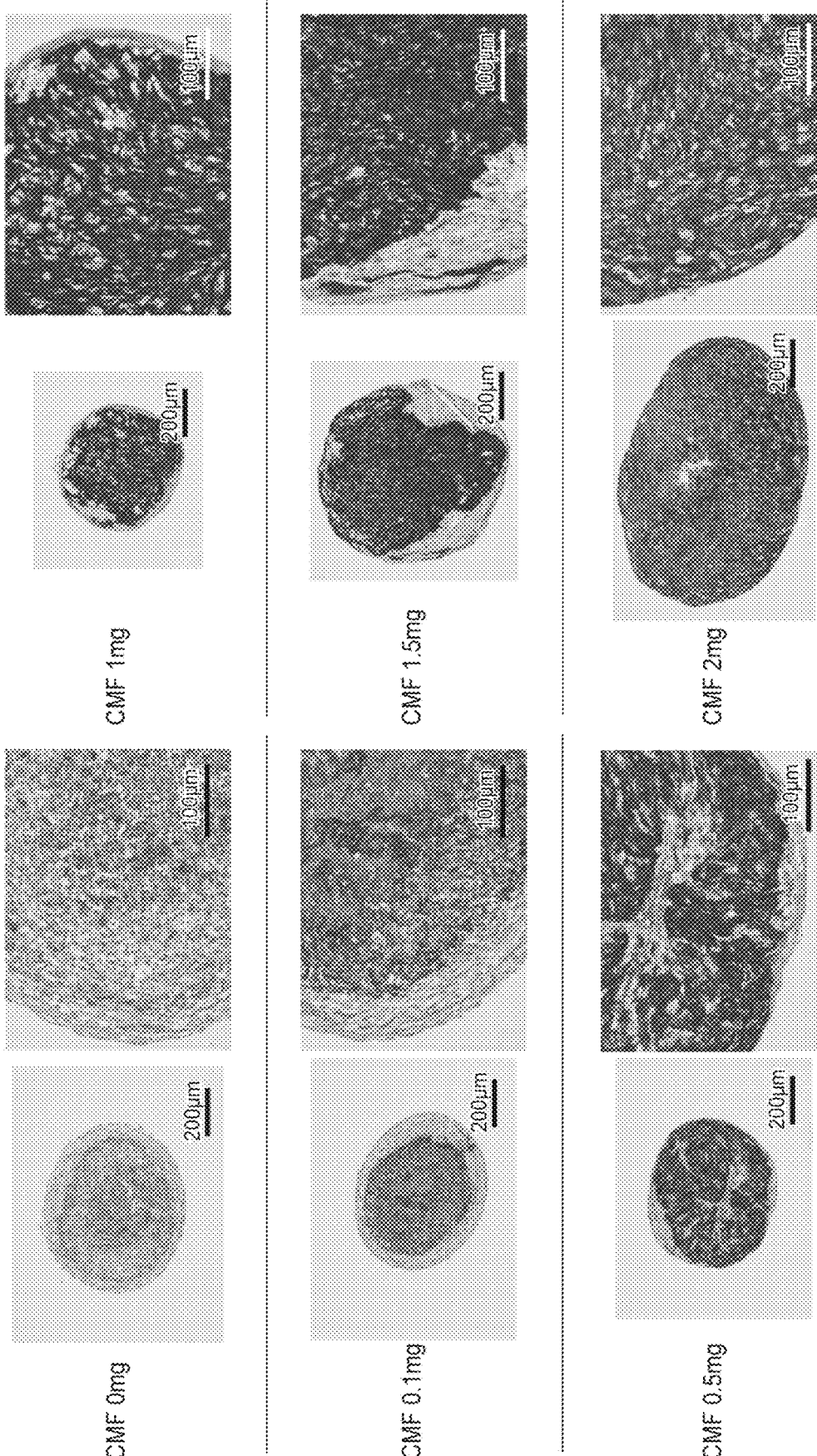
FIG. 15 is Masson's trichrome staining images of three-dimensional tissue bodies including fragmented collagen, human cardiac fibroblasts (NHCFs), and iPS cell-derived cardiomyocytes (iPS-CMs). Each black portion is actually a blue-stained site and indicates the presence of collagen.

The resulting whole three-dimensional tissue was subjected to Masson's trichrome staining ImageJ (created by US National Institute of Health) was used to calculate the area of the whole stained three-dimensional tissue (a cross-section image of substantially the center portion of the spherical body) and the area of blue-stained collagen. The results are shown in Table 2 and FIG. 15. The procedure for calculating the collagen area by ImageJ was specifically conducted as follows. (1) An original color image was subjected to an RGB split by the "Split Channel" command (2) When the whole image was viewed, the "G" image corresponded to the whole tissue area; the "R" image corresponded to the collagen staining area. Then, it was determined that each area was distinguishable. After that, the "G" image and the "R" image were each binarized by the "Threshold" command Regarding each designated threshold at the time of binarization, the "G" image had a threshold of 0 to 75 and the "R" image had a threshold of 0 to 130. (3) The outline of each three-dimensional tissue was designated as an area range by the Selection tool (freehand). Next, the area of each of the (binarized) "G" and "R" images within the range was calculated. Then, the area percentage of the collagen staining area with respect to the whole cross-section of the three-dimensional tissue was estimated.

TABLE 2

| Amount of input CMF (mg) | Whole area (µm²) | Collagen area (µm²) | Percentage of collagen area (%) |
|---|---|---|---|
| 0.0 | 319789 | 23864 | 7.5 |
| 0.1 | 310369 | 99072 | 31.9 |
| 0.5 | 308149 | 206437 | 67 |
| 1.0 | 245054 | 162845 | 66.5 |
| 1.5 | 527522 | 373809 | 70.9 |
| 2.0 | 737304 | 580699 | 78.8 |

As the amount of CMF ("input CMF") used for the production of each three-dimensional tissue was increased, the percentage of the collagen area with respect to the whole three-dimensional tissue increased. However, when the amount of input CMF was 0.5 mg or more, a rate of increase in the percentage of the collagen area was found to decrease. The area percentage should be somewhat affected by the three-dimensional tissue staining protocol and/or the collagen localization state. When determined based on the above procedure, the collagen area was demonstrated to be highly likely to be 50% or more with respect to the at least whole three-dimensional tissue area when 0.5 mg or more of collagen was input.

Example 13: Production of Three-dimensional Tissue by Using Human Cardiac Fibroblasts and Human iPS Cell-derived Cardiomyocytes and Calculation of Collagen Content by Quantification First, 50 mg of lyophilized, pig skin-derived type I collagen manufactured by NH Foods Ltd. was dispersed in 5 mL of 10× phosphate buffered saline (×10 PBS) and was subjected to homogenization using a homogenizer for 6 min to prepare fragmented collagen (CMF). After centrifugation at 3500 rpm for 3 min, a serum-free medium (DMEM) was added. The mixture was washed for 1 min and centrifuged again at 3500 rpm for 3 min to remove the supernatant. A serum-containing medium (DMEM) was then added at a total volume of 5 ml and the fragmented collagen was dispersed.

Next, $5\times10^5$ cells containing human cardiac fibroblasts (NHCFs) and human iPS cell-derived cardiomyocytes (iPS-CMs) at a 25:75 ratio and 1.0 mg of the CMF were mixed at a total liquid volume of 300 µL and were seeded onto a non-adherent 96-well round-bottom plate (the concentration of the solution was calculated as 6.5 mg/mL). After centrifugation at 1100 g for 5 min, the mixture was cultured in an incubator for 3 or 5 days to produce each three-dimensional tissue. The respective samples cultured for 3 days are designated as Day 3-1, Day 3-2, and Day 3-3; and the respective samples cultured for 5 days are designated as Day 5-1, Day 5-2, and Day 5-3.

A QuickZyme Total Collagen Assay (manufactured by QuickZyme Biosciences Inc.) was used to quantify collagen in each three-dimensional tissue by using the following protocol.

(Sample Preparation)

The samples Day 3-1, Day 3-2, Day 3-3, Day 5-1, Day 5-2, and Day 5-3 were each recovered from a non-adherent 96-well round-bottom plate and were lyophilized with a model FDU-2200 (manufactured by TOKYO RIKAKIKAI CO., LTD.). Each whole three-dimensional tissue was mixed with 6 M HCl in each screw cap tube and was incubated in a heat block at 95° C. for 20 h or more. Then, the mixture was returned to room temperature. After centrifugation at 13000 g for 10 min, the supernatant of each sample solution was diluted 10-fold with 6 M HCl. Then, a 200-µL aliquot was diluted with 100 µL of Milli-Q water to prepare each sample. Subsequently, 35 µL of the sample was used.

(Standard Preparation)

First, 125 µL of a standard solution (1200 µg/mL in acetic acid) and 125 µL of 12 M HCl were added to and mixed in a screw cap tube. The tube was incubated in a heat block at 95° C. for 20 h and was then returned to room temperature. After centrifuged at 13000 g for 10 min, the supernatant was diluted with Milli-Q water to prepare S1 at 300 µg/mL. This 51 was serially diluted to prepare S2 (200 µg/mL), S3 (100 µg/mL), S4 (50 µg/mL), S5 (25 µg/mL), S6 (12.5 µg/mL), and S7 (6.25 µg/mL). S8 (0 µg/mL), which contained only 90 µL of 4 M HCl, was also prepared. Here, 35 µl of each was used for experiments.

(Assay)

First, 35 µL of each standard or each sample was added to each well of a plate (coming with QuickZyme Total Collagen Assay kit). Next, 75 µL of an assay buffer (coming with the above kit) was added to each well. The plate was sealed and was then incubated at room temperature while shaking for 20 min. Then, the seal was removed and 75 µL of a detection reagent (reagents A:B=30 µL:45 µL; coming with the above kit) was added to each well. The plate was sealed, and the resulting solution was mixed and incubated at 60° C. for 60 min while shaking. After that, the solution was cooled on ice to room temperature and the seal was removed. Finally, each absorbance at 570 nm was measured. The absorbance of each sample was compared to that of each standard to calculate the amount of collagen. Table 3 shows the results.

TABLE 3

| Sample | Weight of tissue (mg) | Amount of collagen (mg) | Collagen content (wt %) |
|---|---|---|---|
| No collagen | 0.41 | 0.00006 | 0.0 |
| Day 3-1 | 0.57 | 0.2564 | 44.9 |
| Day 3-2 | 0.87 | 0.5474 | 63.3 |
| Day 3-3 | 0.56 | 0.1116 | 20.1 |
| Day 5-1 | 0.42 | 0.2796 | 65.9 |
| Day 5-2 | 0.69 | 0.1446 | 21.1 |
| Day 5-3 | 0.65 | 0.2751 | 42.1 |

The "No collagen" sample indicates a tissue produced in the same conditions as of Day 5 except that no fragmented collagen was used.

The content of collagen in each three-dimensional tissue produced by using fragmented collagen and by culturing for 3 days or 5 days was about 20 to 66% with respect to the dry weight of each corresponding three-dimensional tissue. By contrast, the amount of collagen in the tissue produced without fragmented collagen was 0.06 μg and the content with respect to the three-dimensional tissue was nearly zero.

INDUSTRIAL APPLICABILITY

The present invention makes it possible to produce, at once, a three-dimensional tissue with a thickness of 1 mm or more. In addition, a method for producing a three-dimensional tissue according to the present invention can be used as techniques for producing a reconstructed skin with a structure containing all layers as well as organoids for the liver and the heart in a toxicity model. Further, in a three-dimensional tissue produced using a small number of cardiomyocytes, heart beat synchronous pulsations were observed. Thus, this should be applicable to cardiac toxicity evaluation, etc. Furthermore, a three-dimensional tissue produced using aortic smooth muscle cells should be applicable to an arteriosclerosis blood vessel wall model. Moreover, a three-dimensional tissue produced using gingival fibroblasts may be used for in vitro analysis of periodontitis, etc.

The invention claimed is:

1. A method, comprising:
   bringing cells into contact with a plurality of fragmented collagen pieces derived from exogenous collagen which is exogenous to the cells in an aqueous medium, the bringing of the cells including adding a dispersion of the plurality of fragmented collagen pieces to the aqueous medium containing the cells, or adding the cells to the aqueous medium containing a dispersion of the plurality of fragmented collagen pieces, resulting in a suspension of the cells and the plurality of fragmented collagen pieces in the aqueous medium; and
   culturing the cells with the plurality of fragmented collagen pieces, pieces to form a three-dimensional tissue, the culturing including standing the suspension of the cells and the plurality of fragmented collagen pieces to allow sedimentation, resulting in the plurality of fragmented collagen pieces being uniformly distributed among the cells, three-dimensionally throughout the three-dimensional tissue.

2. The method according to claim 1, wherein the plurality of fragmented collagen pieces have an average length of from 100 nm to 200 μm.

3. The method according to claim 1, wherein the plurality of fragmented collagen pieces have an average diameter of from 50 nm to 30 μm.

4. The method according to claim 1, wherein the cells comprise a collagen-producing cell.

5. The method according to claim 1, wherein the cells comprise one or more types of cells selected from a group of cells consisting of vascular endothelial cells, cancer cells, cardiomyocytes, smooth muscle cells, and epithelial cells.

6. The method according to claim 1, wherein a mass ratio between the plurality of fragmented collagen pieces and the cells is 900:1 to 9:1.

7. The method according to claim 1, wherein collagen in the three-dimensional tissue comprises 10 weight percent (wt %) to 90 wt % based on weight of the three-dimensional tissue.

8. The method according to claim 1, wherein a thickness of the three-dimensional tissue is 10 μm or thicker.

9. The method according to claim 1, further comprising:
   treating the three-dimensional tissue with a trypsin treatment at a trypsin concentration of 0.25%, a temperature of 37° C., and a pH of 7.4 for a reaction time of 15 min.

10. The method according to claim 9, wherein a residual percentage of the three-dimensional tissue after the trypsin treatment is 70% or more, the residual percentage of the three-dimensional tissue is calculated from a mass of the three-dimensional tissue before and after the trypsin treatment.

11. A method comprising:
   bringing cells into contact with a plurality of fragmented collagen pieces in an aqueous medium, the bringing of the cells including adding a dispersion of the plurality of fragmented collagen pieces to the aqueous medium containing the cells, or adding the cells to the aqueous medium containing a dispersion of the plurality of fragmented collagen pieces, resulting in a suspension of the cells and the plurality of fragmented collagen pieces in the aqueous medium;
   culturing the cells with the plurality of fragmented collagen pieces to form a three-dimensional tissue, the culturing including standing the suspension of the cells and the plurality of fragmented collagen pieces to allow sedimentation, resulting in the plurality of fragmented collagen pieces being uniformly distributed among the cells, three-dimensionally throughout the three-dimensional tissue.

12. The method according to claim 11, wherein the plurality of fragmented collagen pieces are exogenous collagen pieces derived from collagen which is exogenous to the cells in the aqueous medium.

13. The method according to claim 11, wherein the plurality of fragmented collagen pieces are concentrated by the sedimentation.

14. The method according to claim 11, wherein the plurality of fragmented collagen pieces have an average length of from 100 nm to 200 μm.

15. The method according to claim 11, wherein the plurality of fragmented collagen pieces have an average diameter of from 50 nm to 30 μm.

16. The method according to claim 11, wherein the cells comprise a collagen-producing cell.

17. The method according to claim 11, wherein a mass ratio between the fragmented collagen pieces and the cells is 900:1 to 9:1.

* * * * *